Figure 1:
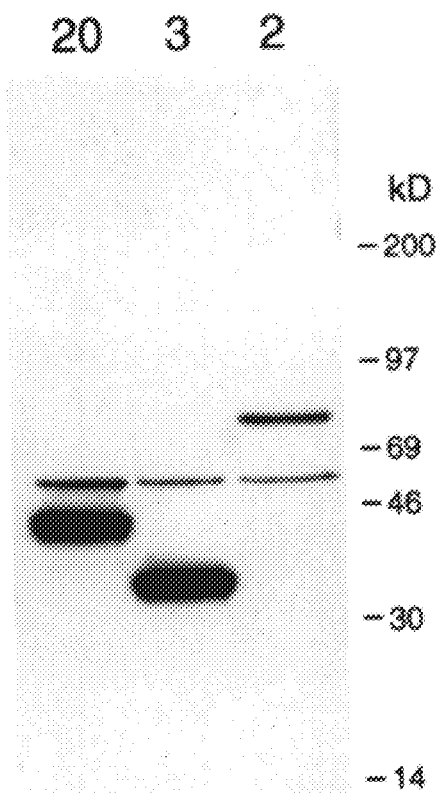

United States Patent [19]
Lin et al.

[11] Patent Number: 5,849,501
[45] Date of Patent: Dec. 15, 1998

[54] TNF RECEPTOR DEATH DOMAIN LIGAND PROTEINS AND METHOD TO IDENTIFY INHIBITORS OF LIGAND BINDING

[75] Inventors: Lih-Ling Lin, Concord; Jennifer Chen, Chestnut Hill; Andrea R. Schievella, Winchester, all of Mass.

[73] Assignee: Genetics Institute, Inc., Cambridge, Mass.

[21] Appl. No.: 494,440

[22] Filed: Jun. 19, 1995

Related U.S. Application Data

[63] Continuation-in-part of Ser. No. 327,514, Oct. 19, 1994, abandoned.

[51] Int. Cl.⁶ .................. G01N 33/566; C07K 14/71; C07K 14/475
[52] U.S. Cl. .................. 435/7.1; 530/300; 530/350; 530/399; 436/501
[58] Field of Search .................. 530/350, 351, 530/388.22, 388.23; 435/7.1, 7.2; 514/2; 436/501

[56] References Cited

U.S. PATENT DOCUMENTS

| | | | |
|---|---|---|---|
| 5,296,592 | 3/1994 | Dower et al. | 530/4.3 |
| 5,464,938 | 11/1995 | Smith et al. | 530/350 |
| 5,506,340 | 4/1996 | Heavner | 530/324 |
| 5,563,039 | 10/1996 | Goeddel et al. | 435/7.1 |

FOREIGN PATENT DOCUMENTS

| | | |
|---|---|---|
| A-46127/93 | 9/1993 | Australia . |
| 308378 | 3/1989 | European Pat. Off. . |
| 433900 | 6/1991 | European Pat. Off. . |
| 526905 | 2/1993 | European Pat. Off. . |
| 0 585 939 A2 | 9/1993 | European Pat. Off. . |
| WO 92/03470 | 3/1992 | WIPO . |
| WO 92/03471 | 3/1992 | WIPO . |
| WO 92/14834 | 9/1992 | WIPO . |
| WO 93/19777 | 10/1993 | WIPO . |
| WO 94/01548 | 1/1994 | WIPO . |
| WO 94/10207 | 5/1994 | WIPO . |
| WO 95/31544 | 11/1995 | WIPO . |
| WO 95/33051 | 12/1995 | WIPO . |
| 96/25941 | 8/1996 | WIPO . |

OTHER PUBLICATIONS

Miki et al. (1992) Cancer Res. 52:643.
Darnay et al. (1994) J. Biol. Chem. 269:20299.
Kiefer et al. (1992) J. Biol. Chem. 267:12692.
Genbank accession No. T08593 (1993).
Genbank accession No. T07800 (1993).
Genbank accession No. M78050 (1992).
Genbank accession No. M78539 (1992).
Luban and Goff, 1995, Curr. Open. Biotech. 6:59–64.
GenBank Accession No. U44953; 1 Jul. 1996.
GenBank Accession No. U48254; 3 Aug. 1996.
Schall et al., Cell 61:361–370 (1990).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Gyuris et al., Cell 75:791–803 (1993).
Gietz et al., Nucleic Acids Res. 20:1425 (1992).
Waye et al., Protein Engineering 8:90 (1995).
Auffray et al., Life Sciences 318:263–272 (1995).
Rothe et al., Cell 78:681–692 (1994).
Song et al., The Journal of Biological Chemistry 269:22492–22495 (1994).
Tartaglia et al., Cell 74:845–853 (1993).
Boldin et al., The Journal of Biological Chemistry 270(1):387–391 (1995).
Hsu et al., Cell 81:495–504 (1995).
Boldin et al., FEBS Letters 367:39–44 (1995).
Tartaglia et al., Tumor necrosis factor receptor signaling, J. Biol. Chem., 267(7): 4304–4307, Mar. 1992.
Tartaglia et al., Tumor necrosis factor's cytotoxic activity is signaled by the p55 TNF receptor, Cell, 73: 213–216, Apr. 1993.

*Primary Examiner*—Stephen Walsh
*Assistant Examiner*—Claire M. Kaufman
*Attorney, Agent, or Firm*—Scott A. Brown; Suzanne A. Sprunger; Thomas J. DesRosier

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

6 Claims, 6 Drawing Sheets

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 2158 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS ( B ) LOCATION: 2..1231

( x i ) SEQUENCE DESCRIPTION: SEQ ID NO:1:

```
C AGC AAT GCA GGT GAT GGA CCA GGT GGC GAG GGC AGT GTT CAC CTG          46
  Ser Asn Ala Gly Asp Gly Pro Gly Gly Glu Gly Ser Val His Leu
  1               5                   10                  15

GCA AGC TCT CGG GGC ACT TTG TCT GAT AGT GAA ATT GAG ACC AAC TCT          94
Ala Ser Ser Arg Gly Thr Leu Ser Asp Ser Glu Ile Glu Thr Asn Ser
                20                  25                  30

GCC ACA AGC ACC ATC TTT GGT AAA GCC CAC AGC TTG AAG CCA AGC ATA         142
Ala Thr Ser Thr Ile Phe Gly Lys Ala His Ser Leu Lys Pro Ser Ile
            35                  40                  45

AAG GAG AAG CTG GCA GGC AGC CCC ATT CGT ACT TCT GAA GAT GTG AGC         190
Lys Glu Lys Leu Ala Gly Ser Pro Ile Arg Thr Ser Glu Asp Val Ser
        50                  55                  60

CAG CGA GTC TAT CTC TAT GAG GGA CTC CTA GGC AAA GAG CGT TCT ACT         238
Gln Arg Val Tyr Leu Tyr Glu Gly Leu Leu Gly Lys Glu Arg Ser Thr
    65                  70                  75

TTA TGG GAC CAA ATG CAA TTC TGG GAA GAT GCC TTC TTA GAT GCT GTG         286
Leu Trp Asp Gln Met Gln Phe Trp Glu Asp Ala Phe Leu Asp Ala Val
80                  85                  90                  95

ATG TTG GAG AGA GAA GGG ATG GGT ATG GAC CAG GGT CCC CAG GAA ATG         334
Met Leu Glu Arg Glu Gly Met Gly Met Asp Gln Gly Pro Gln Glu Met
                100                 105                 110

ATC GAC AGG TAC CTG TCC CTT GGA GAA CAT GAC CGG AAG CGC CTG GAA         382
Ile Asp Arg Tyr Leu Ser Leu Gly Glu His Asp Arg Lys Arg Leu Glu
            115                 120                 125

GAT GAT GAA GAT CGC TTG CTG GCC ACA CTT CTG CAC AAC CTC ATC TCC         430
Asp Asp Glu Asp Arg Leu Leu Ala Thr Leu Leu His Asn Leu Ile Ser
        130                 135                 140

TAC ATG CTG CTG ATG AAG GTA AAT AAG AAT GAC ATC CGC AAG AAG GTG         478
Tyr Met Leu Leu Met Lys Val Asn Lys Asn Asp Ile Arg Lys Lys Val
    145                 150                 155

AGG CGC CTA ATG GGA AAG TCG CAC ATT GGG CTT GTG TAC AGC CAG CAA         526
Arg Arg Leu Met Gly Lys Ser His Ile Gly Leu Val Tyr Ser Gln Gln
160                 165                 170                 175

ATC AAT GAG GTG CTT GAT CAG CTG GCG AAC CTG AAT GGA CGC GAT CTC         574
Ile Asn Glu Val Leu Asp Gln Leu Ala Asn Leu Asn Gly Arg Asp Leu
                180                 185                 190

TCT ATC TGG TCC AGT GGC AGC CGG CAC ATG AAG AAG CAG ACA TTT GTG         622
Ser Ile Trp Ser Ser Gly Ser Arg His Met Lys Lys Gln Thr Phe Val
            195                 200                 205

GTA CAT GCA GGG ACA GAT ACA AAC GGA GAT ATC TTT TTC ATG GAG GTG         670
Val His Ala Gly Thr Asp Thr Asn Gly Asp Ile Phe Phe Met Glu Val
        210                 215                 220

TGC GAT GAC TGT GTG GTG TTG CGT AGT AAC ATC GGA ACA GTG TAT GAG         718
Cys Asp Asp Cys Val Val Leu Arg Ser Asn Ile Gly Thr Val Tyr Glu
    225                 230                 235

CGC TGG TGG TAC GAG AAG CTC ATC AAC ATG ACC TAC TGT CCC AAG ACG         766
Arg Trp Trp Tyr Glu Lys Leu Ile Asn Met Thr Tyr Cys Pro Lys Thr
240                 245                 250                 255

AAG GTG TTG TGC TTG TGG CGT AGA AAT GGC TCT GAG ACC CAG CTC AAC         814
Lys Val Leu Cys Leu Trp Arg Arg Asn Gly Ser Glu Thr Gln Leu Asn
                260                 265                 270

AAG TTC TAT ACT AAA AAG TGT CGG GAG CTG TAC TAC TGT GTG AAG GAC         862
Lys Phe Tyr Thr Lys Lys Cys Arg Glu Leu Tyr Tyr Cys Val Lys Asp
            275                 280                 285

AGC ATG GAG CGC GCT GCC GCC CGA CAG CAA AGC ATC AAA CCC GGA CCT         910
Ser Met Glu Arg Ala Ala Ala Arg Gln Gln Ser Ile Lys Pro Gly Pro
        290                 295                 300
```

-continued

```
GAA TTG GGT GGC GAG TTC CCT GTG CAG GAC CTG AAG ACT GGT GAG GGT    958
Glu Leu Gly Gly Glu Phe Pro Val Gln Asp Leu Lys Thr Gly Glu Gly
    305                 310                 315

GGC CTG CTG CAG GTG ACC CTG GAA GGG ATC AAC CTC AAA TTC ATG CAC   1006
Gly Leu Leu Gln Val Thr Leu Glu Gly Ile Asn Leu Lys Phe Met His
320                 325                 330                 335

AAT CAG GTT TTC ATA GAG CTG AAT CAC ATT AAA AAG TGC AAT ACA GTT   1054
Asn Gln Val Phe Ile Glu Leu Asn His Ile Lys Lys Cys Asn Thr Val
                340                 345                 350

CGA GGC GTC TTT GTC CTG GAG GAA TTT GTT CCT GAA ATT AAA GAA GTG   1102
Arg Gly Val Phe Val Leu Glu Glu Phe Val Pro Glu Ile Lys Glu Val
                355                 360                 365

GTG AGC CAC AAG TAC AAG ACA CCA ATG GCC CAC GAA ATC TGC TAC TCC   1150
Val Ser His Lys Tyr Lys Thr Pro Met Ala His Glu Ile Cys Tyr Ser
        370                 375                 380

GTA TTA TGT CTC TTC TCG TAC GTG GCT GCA GTT CAT AGC AGT GAG GAA   1198
Val Leu Cys Leu Phe Ser Tyr Val Ala Ala Val His Ser Ser Glu Glu
385                 390                 395

GAT CTC AGA ACC CCG CCC CGG CCT GTC TCT AGC TGATGGAGAG GGGCTACGCA  1251
Asp Leu Arg Thr Pro Pro Arg Pro Val Ser Ser
400                 405                 410

GCTGCCCCAG CCCAGGGCAC GCCCCTGGCC CCTTGCTGTT CCCAAGTGCA CGATGCTGCT  1311
GTGACTGAGG AGTGGATGAT GCTCGTGTGT CCTCTGCAAG CCCCCTGCTG TGGCTTGGGT  1371
GGGTACCGGT TATGTGTCCC TCTGAGTGTG TCTTGAGCGT GTCCACCTTC TCCCTCTCCA  1431
CTCCCAGAAG ACCAAACTGC CTTCCCCTCA GGGCTCAAGA ATGTGTACAG TCTGTGGGGC  1491
CGGTGTGAAC CCACTATTTT GTGTCCTTGA CACATTTGTG TTGTGGTTCC TTGTCCTTGT  1551
CCCTGGCGTT AACTGTCCAC TGCAAGAGTC TGGCTCTCCC TTCTCTGTGA CCCGGCATGA  1611
CTGGGCGCCT GGAGCAGTTT CACTCTGTGA GGAGTGAGGG AACCCTGGGG CTCACCCTCT  1671
CAGAGGAAGG GCACAGAGAG GAAGGGAAGA ATTGGGGGGC AGCCGGAGTG AGTGGCAGCC  1731
TCCCTGCTTC CTTCTGCATT CCCAAGCCGG CAGCTACTGC CCAGGGCCCG CAGTGTTGGC  1791
TGCTGCCTGC CACAGCCTCT GTGACTGCAG TGGAGCGGCG AATTCCCTGT GGCCTGCCAC  1851
GCCTTCGGCA TCAGAGGATG GAGTGGTCGA GGCTAGTGGA GTCCCAGGGA CCGCTGGCTG  1911
CTCTGCCTGA GCATCAGGGA GGGGGCAGGA AGACCAAGC TGGGTTTGCA CATCTGTCTG   1971
CAGGCTGTCT CTCCAGGCAC GGGGTGTCAG GAGGGAGAGA CAGCCTGGGT ATGGGCAAGA  2031
AATGACTGTA AATATTTCAG CCCCACATTA TTTATAGAAA ATGTACAGTT GTGTGAATGT  2091
GAAATAAATG TCCTCACCTC CCAAAAAAAA AAAAAAAAAA AAAAAAAAAA AAAAAAAAAA  2151
AAAAAAA                                                            2158
```

( 2 ) INFORMATION FOR SEQ ID NO:2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Ser Asn Ala Gly Asp Gly Pro Gly Gly Glu Gly Ser Val His Leu Ala
1               5                   10                  15

Ser Ser Arg Gly Thr Leu Ser Asp Ser Glu Ile Glu Thr Asn Ser Ala
                20                  25                  30

Thr Ser Thr Ile Phe Gly Lys Ala His Ser Leu Lys Pro Ser Ile Lys
            35                  40                  45
```

| | | | | | | | | | | | | | | |
|---|---|---|---|---|---|---|---|---|---|---|---|---|---|---|
| Glu | Lys | Leu | Ala | Gly | Ser | Pro | Ile | Arg | Thr | Ser | Glu | Asp | Val | Ser | Gln |
| | 50 | | | | | 55 | | | | | 60 | | | | |
| Arg | Val | Tyr | Leu | Tyr | Glu | Gly | Leu | Leu | Gly | Lys | Glu | Arg | Ser | Thr | Leu |
| 65 | | | | | 70 | | | | | 75 | | | | | 80 |
| Trp | Asp | Gln | Met | Gln | Phe | Trp | Glu | Asp | Ala | Phe | Leu | Asp | Ala | Val | Met |
| | | | | 85 | | | | | 90 | | | | | 95 | |
| Leu | Glu | Arg | Glu | Gly | Met | Gly | Met | Asp | Gln | Gly | Pro | Gln | Glu | Met | Ile |
| | | | 100 | | | | | 105 | | | | | 110 | | |
| Asp | Arg | Tyr | Leu | Ser | Leu | Gly | Glu | His | Asp | Arg | Lys | Arg | Leu | Glu | Asp |
| | | 115 | | | | | 120 | | | | | 125 | | | |
| Asp | Glu | Asp | Arg | Leu | Leu | Ala | Thr | Leu | Leu | His | Asn | Leu | Ile | Ser | Tyr |
| | 130 | | | | | 135 | | | | | 140 | | | | |
| Met | Leu | Leu | Met | Lys | Val | Asn | Lys | Asn | Asp | Ile | Arg | Lys | Lys | Val | Arg |
| 145 | | | | | 150 | | | | | 155 | | | | | 160 |
| Arg | Leu | Met | Gly | Lys | Ser | His | Ile | Gly | Leu | Val | Tyr | Ser | Gln | Gln | Ile |
| | | | | 165 | | | | | 170 | | | | | 175 | |
| Asn | Glu | Val | Leu | Asp | Gln | Leu | Ala | Asn | Leu | Asn | Gly | Arg | Asp | Leu | Ser |
| | | | 180 | | | | | 185 | | | | | 190 | | |
| Ile | Trp | Ser | Ser | Gly | Ser | Arg | His | Met | Lys | Lys | Gln | Thr | Phe | Val | Val |
| | | 195 | | | | | 200 | | | | | 205 | | | |
| His | Ala | Gly | Thr | Asp | Thr | Asn | Gly | Asp | Ile | Phe | Phe | Met | Glu | Val | Cys |
| | 210 | | | | | 215 | | | | | 220 | | | | |
| Asp | Asp | Cys | Val | Val | Leu | Arg | Ser | Asn | Ile | Gly | Thr | Val | Tyr | Glu | Arg |
| 225 | | | | | 230 | | | | | 235 | | | | | 240 |
| Trp | Trp | Tyr | Glu | Lys | Leu | Ile | Asn | Met | Thr | Tyr | Cys | Pro | Lys | Thr | Lys |
| | | | | 245 | | | | | 250 | | | | | 255 | |
| Val | Leu | Cys | Leu | Trp | Arg | Arg | Asn | Gly | Ser | Glu | Thr | Gln | Leu | Asn | Lys |
| | | | 260 | | | | | 265 | | | | | 270 | | |
| Phe | Tyr | Thr | Lys | Lys | Cys | Arg | Glu | Leu | Tyr | Tyr | Cys | Val | Lys | Asp | Ser |
| | | 275 | | | | | 280 | | | | | 285 | | | |
| Met | Glu | Arg | Ala | Ala | Ala | Arg | Gln | Gln | Ser | Ile | Lys | Pro | Gly | Pro | Glu |
| | 290 | | | | | 295 | | | | | 300 | | | | |
| Leu | Gly | Gly | Glu | Phe | Pro | Val | Gln | Asp | Leu | Lys | Thr | Gly | Glu | Gly | Gly |
| 305 | | | | | 310 | | | | | 315 | | | | | 320 |
| Leu | Leu | Gln | Val | Thr | Leu | Glu | Gly | Ile | Asn | Leu | Lys | Phe | Met | His | Asn |
| | | | | 325 | | | | | 330 | | | | | 335 | |
| Gln | Val | Phe | Ile | Glu | Leu | Asn | His | Ile | Lys | Lys | Cys | Asn | Thr | Val | Arg |
| | | | 340 | | | | | 345 | | | | | 350 | | |
| Gly | Val | Phe | Val | Leu | Glu | Glu | Phe | Val | Pro | Glu | Ile | Lys | Glu | Val | Val |
| | | 355 | | | | | 360 | | | | | 365 | | | |
| Ser | His | Lys | Tyr | Lys | Thr | Pro | Met | Ala | His | Glu | Ile | Cys | Tyr | Ser | Val |
| | 370 | | | | | 375 | | | | | 380 | | | | |
| Leu | Cys | Leu | Phe | Ser | Tyr | Val | Ala | Ala | Val | His | Ser | Ser | Glu | Glu | Asp |
| 385 | | | | | 390 | | | | | 395 | | | | | 400 |
| Leu | Arg | Thr | Pro | Pro | Arg | Pro | Val | Ser | Ser | | | | | | |
| | | | | 405 | | | | | 410 | | | | | | |

( 2 ) INFORMATION FOR SEQ ID NO:3:

( i ) SEQUENCE CHARACTERISTICS:
        ( A ) LENGTH: 826 base pairs
        ( B ) TYPE: nucleic acid
        ( C ) STRANDEDNESS: double
        ( D ) TOPOLOGY: linear ( i i ) MOLECULE TYPE: cDNA (i i i) HYPOTHETICAL: NO (i x) FEATURE:
(A) NAME/KEY: CDS
(B) LOCATION: 2..415

(x i) SEQUENCE DESCRIPTION: SEQ ID NO:3:

```
G GAG GTG CAG GAC CTC TTC GAA GCC CAG GGC AAT GAC CGA CTG AAG        46
  Glu Val Gln Asp Leu Phe Glu Ala Gln Gly Asn Asp Arg Leu Lys
   1               5                  10                  15

CTG CTG GTG CTG TAC AGT GGA GAG GAT GAT GAG CTG CTA CAG CGG GCA      94
Leu Leu Val Leu Tyr Ser Gly Glu Asp Asp Glu Leu Leu Gln Arg Ala
                    20                  25                  30

GCT GCC GGG GGC TTG GCC ATG CTT ACC TCC ATG CGG CCC ACG CTC TGC     142
Ala Ala Gly Gly Leu Ala Met Leu Thr Ser Met Arg Pro Thr Leu Cys
                35                      40                  45

AGC CGC ATT CCC CAA GTG ACC ACA CAC TGG CTG GAG ATC CTG CAG GCC     190
Ser Arg Ile Pro Gln Val Thr Thr His Trp Leu Glu Ile Leu Gln Ala
            50                  55                  60

CTG CTT CTG AGC TCC AAC CAG GAG CTG CAG CAC CGG GGT GCT GTG GTG     238
Leu Leu Leu Ser Ser Asn Gln Glu Leu Gln His Arg Gly Ala Val Val
        65                  70                  75

GTG CTG AAC ATG GTG GAG GCC TCG AGG GAG ATT GCC AGC ACC CTG ATG     286
Val Leu Asn Met Val Glu Ala Ser Arg Glu Ile Ala Ser Thr Leu Met
 80                  85                  90                  95

GAG AGT GAG ATG ATG GAG ATC TTG TCA GTG CTA GCT AAG GGT GAC CAC     334
Glu Ser Glu Met Met Glu Ile Leu Ser Val Leu Ala Lys Gly Asp His
                100                 105                 110

AGC CCT GTC ACA AGG GCT GCT GCA GCC TGC CTG GAC AAA GCA GTG GAA     382
Ser Pro Val Thr Arg Ala Ala Ala Ala Cys Leu Asp Lys Ala Val Glu
            115                 120                 125

TAT GGG CTT ATC CAA CCC AAC CAA GAT GGA GAG TGAGGGGGTT GTCCCTGGGC   435
Tyr Gly Leu Ile Gln Pro Asn Gln Asp Gly Glu
            130                 135

CCAAGGCTCA TGCACACGCT ACCTATTGTG GCACGGAGAG TAAGGACGGA AGCAGCTTTG   495
GCTGGTGGTG GCTGGCATGC CCAATACTCT TGCCCATCCT CGCTTGCTGC CCTAGGATGT   555
CCTCTGTTCT GAGTCAGCGG CCACGTTCAG TCACACAGCC CTGCTTGGCC AGCACTGCCT   615
GCAGCCTCAC TCAGAGGGGC CCTTTTTCTG TACTACTGTA GTCAGCTGGG AATGGGGAAG   675
GTGCATCCCA ACACAGCCTG TGGATCCTGG GGCATTTGGA AGGGCGCACA CATCAGCAGC   735
CTCACCAGCT GTGAGCCTGC TATCAGGCCT GCCCCTCCAA TAAAAGTGTG TAGAACTCCA   795
AAAAAAAAAA AAAAAAAAA AAAAAAAAA A                                   826
```

(2) INFORMATION FOR SEQ ID NO:4:

(i) SEQUENCE CHARACTERISTICS:
(A) LENGTH: 138 amino acids
(B) TYPE: amino acid
(D) TOPOLOGY: linear (i i) MOLECULE TYPE: protein (x i) SEQUENCE DESCRIPTION: SEQ ID NO:4:

```
Glu Val Gln Asp Leu Phe Glu Ala Gln Gly Asn Asp Arg Leu Lys Leu
 1               5                  10                  15

Leu Val Leu Tyr Ser Gly Glu Asp Asp Glu Leu Leu Gln Arg Ala Ala
                20                  25                  30

Ala Gly Gly Leu Ala Met Leu Thr Ser Met Arg Pro Thr Leu Cys Ser
            35                  40                  45
```

```
Arg  Ile  Pro  Gln  Val  Thr  Thr  His  Trp  Leu  Glu  Ile  Leu  Gln  Ala  Leu
          50                       55                      60

Leu  Leu  Ser  Ser  Asn  Gln  Glu  Leu  Gln  His  Arg  Gly  Ala  Val  Val  Val
65                       70                       75                           80

Leu  Asn  Met  Val  Glu  Ala  Ser  Arg  Glu  Ile  Ala  Ser  Thr  Leu  Met  Glu
                    85                       90                       95

Ser  Glu  Met  Met  Glu  Ile  Leu  Ser  Val  Leu  Ala  Lys  Gly  Asp  His  Ser
               100                      105                     110

Pro  Val  Thr  Arg  Ala  Ala  Ala  Ala  Cys  Leu  Asp  Lys  Ala  Val  Glu  Tyr
               115                      120                     125

Gly  Leu  Ile  Gln  Pro  Asn  Gln  Asp  Gly  Glu
          130                      135
```

( 2 ) INFORMATION FOR SEQ ID NO:5:

( i ) SEQUENCE CHARACTERISTICS:
        ( A ) LENGTH: 722 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..559

( x i ) SEQUENCE DESCRIPTION: SEQ ID NO:5:

```
G  GAG  AAG  CCG  CTG  CAC  GCC  CTG  CTG  CAC  GGC  CGC  GGG  GTT  TGC  CTC         46
   Glu  Lys  Pro  Leu  His  Ala  Leu  Leu  His  Gly  Arg  Gly  Val  Cys  Leu
    1              5                        10                       15

AAC  GAA  AAG  AGC  TAC  CGC  GAG  CAA  GTC  AAG  ATC  GAG  AGA  GAC  TCC  CGT        94
Asn  Glu  Lys  Ser  Tyr  Arg  Glu  Gln  Val  Lys  Ile  Glu  Arg  Asp  Ser  Arg
               20                       25                       30

GAG  CAC  GAG  GAG  CCC  ACC  ACC  TCT  GAG  ATG  GCC  GAG  GAG  ACC  TAC  TCC      142
Glu  His  Glu  Glu  Pro  Thr  Thr  Ser  Glu  Met  Ala  Glu  Glu  Thr  Tyr  Ser
                35                       40                       45

CCC  AAG  ATC  TTC  CGG  CCC  AAA  CAC  ACC  CGC  ATC  TCC  GAG  CTG  AAG  GCT      190
Pro  Lys  Ile  Phe  Arg  Pro  Lys  His  Thr  Arg  Ile  Ser  Glu  Leu  Lys  Ala
          50                       55                       60

GAA  GCA  GTG  AAG  AAG  GAC  CGC  AGA  AAG  AAG  CTG  ACC  CAG  TCC  AAG  TTT      238
Glu  Ala  Val  Lys  Lys  Asp  Arg  Arg  Lys  Lys  Leu  Thr  Gln  Ser  Lys  Phe
     65                       70                       75

GTC  GGG  GGA  GCC  GAG  AAC  ACT  GCC  CAC  CCC  CGG  ATC  ATC  TCT  GAA  CCT      286
Val  Gly  Gly  Ala  Glu  Asn  Thr  Ala  His  Pro  Arg  Ile  Ile  Ser  Glu  Pro
80                       85                       90                       95

GAG  ATG  AGA  CAG  GAG  TCT  GAG  CAG  GGC  CCC  TGC  CGC  AGA  CAC  ATG  GAG      334
Glu  Met  Arg  Gln  Glu  Ser  Glu  Gln  Gly  Pro  Cys  Arg  Arg  His  Met  Glu
                    100                      105                     110

GCT  TCC  CTG  CAG  GAG  CTC  AAA  GCC  AGC  CCA  CGC  ATG  GTG  CCC  CGT  GCT      382
Ala  Ser  Leu  Gln  Glu  Leu  Lys  Ala  Ser  Pro  Arg  Met  Val  Pro  Arg  Ala
               115                      120                     125

GTG  TAC  CTG  CCC  AAT  TGT  GAC  CGC  AAA  GGA  TTC  TAC  AAG  AGA  AAG  CAG      430
Val  Tyr  Leu  Pro  Asn  Cys  Asp  Arg  Lys  Gly  Phe  Tyr  Lys  Arg  Lys  Gln
          130                      135                     140

TGC  AAA  CCT  TCC  CGT  GGC  CGC  AAG  CGT  GGC  ATC  TGC  TGG  TGC  GTG  GAC      478
Cys  Lys  Pro  Ser  Arg  Gly  Arg  Lys  Arg  Gly  Ile  Cys  Trp  Cys  Val  Asp
     145                      150                     155

AAG  TAC  GGG  ATG  AAG  CTG  CCA  GGC  ATG  GAG  TAC  GTT  GAC  GGG  GAC  TTT      526
Lys  Tyr  Gly  Met  Lys  Leu  Pro  Gly  Met  Glu  Tyr  Val  Asp  Gly  Asp  Phe
160                      165                      170                     175
```

```
       CAG TGC CAC ACC TTC GAC AGC AGC AAC GTT GAG TGATGCGTCC CCCCCCAACC      579
       Gln Cys His Thr Phe Asp Ser Ser Asn Val Glu
                       180                 185

TTTCCCTCAC CCCCTTCCAC CCCCAGCCCC GACTCCAGCC AGCGCCTCCC TCCACCCCAG      639

GACGCCACTC ATTTCATCTC ATTTAAGGGA AAAATATATA TCTATCTATT TGAGGAAAAA      699

AAAAAAAAAA AAAAAAAAA AAA                                               722
```

( 2 ) INFORMATION FOR SEQ ID NO:6:

( i ) SEQUENCE CHARACTERISTICS:
        ( A ) LENGTH: 186 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Glu Lys Pro Leu His Ala Leu Leu His Gly Arg Gly Val Cys Leu Asn
 1               5                  10                  15

Glu Lys Ser Tyr Arg Glu Gln Val Lys Ile Glu Arg Asp Ser Arg Glu
            20                  25                  30

His Glu Glu Pro Thr Thr Ser Glu Met Ala Glu Glu Thr Tyr Ser Pro
        35                  40                  45

Lys Ile Phe Arg Pro Lys His Thr Arg Ile Ser Glu Leu Lys Ala Glu
    50                  55                  60

Ala Val Lys Lys Asp Arg Arg Lys Lys Leu Thr Gln Ser Lys Phe Val
65                  70                  75                  80

Gly Gly Ala Glu Asn Thr Ala His Pro Arg Ile Ile Ser Glu Pro Glu
                85                  90                  95

Met Arg Gln Glu Ser Glu Gln Gly Pro Cys Arg Arg His Met Glu Ala
               100                 105                 110

Ser Leu Gln Glu Leu Lys Ala Ser Pro Arg Met Val Pro Arg Ala Val
           115                 120                 125

Tyr Leu Pro Asn Cys Asp Arg Lys Gly Phe Tyr Lys Arg Lys Gln Cys
    130                 135                 140

Lys Pro Ser Arg Gly Arg Lys Arg Gly Ile Cys Trp Cys Val Asp Lys
145                 150                 155                 160

Tyr Gly Met Lys Leu Pro Gly Met Glu Tyr Val Asp Gly Asp Phe Gln
                165                 170                 175

Cys His Thr Phe Asp Ser Ser Asn Val Glu
                180                 185
```

( 2 ) INFORMATION FOR SEQ ID NO:7:

( i ) SEQUENCE CHARACTERISTICS:
        ( A ) LENGTH: 1023 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 57..875

( x i ) SEQUENCE DESCRIPTION: SEQ ID NO:7:

```
CCCTGCACTC TCGCTCTCCT GCCCCACCCC GAGGTAAAGG GGGCGACTAA GAGAAG            56
```

| | | | | | | | | | | | | | | | | |
|---|---|---|---|---|---|---|---|---|---|---|---|---|---|---|---|---|
| ATG | GTG | TTG | CTC | ACC | GCG | GTC | CTC | CTG | CTG | CTG | GCC | GCC | TAT | GCG | GGG | 104 |
| Met | Val | Leu | Leu | Thr | Ala | Val | Leu | Leu | Leu | Leu | Ala | Ala | Tyr | Ala | Gly | |
| 1 | | | | 5 | | | | | 10 | | | | | 15 | | |
| CCG | GCC | CAG | AGC | CTG | GGC | TCC | TTC | GTG | CAC | TGC | GAG | CCC | TGC | GAC | GAG | 152 |
| Pro | Ala | Gln | Ser | Leu | Gly | Ser | Phe | Val | His | Cys | Glu | Pro | Cys | Asp | Glu | |
| | | | 20 | | | | | 25 | | | | | 30 | | | |
| AAA | GCC | CTC | TCC | ATG | TGC | CCC | CCC | AGC | CCC | CTG | GGC | TGC | GAG | CTG | GTC | 200 |
| Lys | Ala | Leu | Ser | Met | Cys | Pro | Pro | Ser | Pro | Leu | Gly | Cys | Glu | Leu | Val | |
| | | 35 | | | | | 40 | | | | | 45 | | | | |
| AAG | GAG | CCG | GGC | TGC | GGC | TGC | TGC | ATG | ACC | TGC | GCC | CTG | GCC | GAG | GGG | 248 |
| Lys | Glu | Pro | Gly | Cys | Gly | Cys | Cys | Met | Thr | Cys | Ala | Leu | Ala | Glu | Gly | |
| | 50 | | | | 55 | | | | | 60 | | | | | | |
| CAG | TCG | TGC | GGC | GTC | TAC | ACC | GAG | CGC | TGC | GCC | CAG | GGG | CTG | CGC | TGC | 296 |
| Gln | Ser | Cys | Gly | Val | Tyr | Thr | Glu | Arg | Cys | Ala | Gln | Gly | Leu | Arg | Cys | |
| 65 | | | | 70 | | | | | 75 | | | | | 80 | | |
| CTC | CCC | CGG | CAG | GAC | GAG | GAG | AAG | CCG | CTG | CAC | GCC | CTG | CTG | CAC | GGC | 344 |
| Leu | Pro | Arg | Gln | Asp | Glu | Glu | Lys | Pro | Leu | His | Ala | Leu | Leu | His | Gly | |
| | | | | 85 | | | | | 90 | | | | | 95 | | |
| CGC | GGG | GTT | TGC | CTC | AAC | GAA | AAG | AGC | TAC | CGC | GAG | CAA | GTC | AAG | ATC | 392 |
| Arg | Gly | Val | Cys | Leu | Asn | Glu | Lys | Ser | Tyr | Arg | Glu | Gln | Val | Lys | Ile | |
| | | | 100 | | | | | 105 | | | | | 110 | | | |
| GAG | AGA | GAC | TCC | CGT | GAG | CAC | GAG | GAG | CCC | ACC | ACC | TCT | GAG | ATG | GCC | 440 |
| Glu | Arg | Asp | Ser | Arg | Glu | His | Glu | Glu | Pro | Thr | Thr | Ser | Glu | Met | Ala | |
| | | 115 | | | | | 120 | | | | | 125 | | | | |
| GAG | GAG | ACC | TAC | TCC | CCC | AAG | ATC | TTC | CGG | CCC | AAA | CAC | ACC | CGC | ATC | 488 |
| Glu | Glu | Thr | Tyr | Ser | Pro | Lys | Ile | Phe | Arg | Pro | Lys | His | Thr | Arg | Ile | |
| | 130 | | | | | 135 | | | | | 140 | | | | | |
| TCC | GAG | CTG | AAG | GCT | GAA | GCA | GTG | AAG | AAG | GAC | CGC | AGA | AAG | AAG | CTG | 536 |
| Ser | Glu | Leu | Lys | Ala | Glu | Ala | Val | Lys | Lys | Asp | Arg | Arg | Lys | Lys | Leu | |
| 145 | | | | | 150 | | | | | 155 | | | | | 160 | |
| ACC | CAG | TCC | AAG | TTT | GTC | GGG | GGA | GCC | GAG | AAC | ACT | GCC | CAC | CCC | CGG | 584 |
| Thr | Gln | Ser | Lys | Phe | Val | Gly | Gly | Ala | Glu | Asn | Thr | Ala | His | Pro | Arg | |
| | | | | 165 | | | | | 170 | | | | | 175 | | |
| ATC | ATC | TCT | GCA | CCT | GAG | ATG | AGA | CAG | GAG | TCT | GAG | CAG | GGC | CCC | TGC | 632 |
| Ile | Ile | Ser | Ala | Pro | Glu | Met | Arg | Gln | Glu | Ser | Glu | Gln | Gly | Pro | Cys | |
| | | | 180 | | | | | 185 | | | | | 190 | | | |
| CGC | AGA | CAC | ATG | GAG | GCT | TCC | CTG | CAG | GAG | CTC | AAA | GCC | AGC | CCA | CGC | 680 |
| Arg | Arg | His | Met | Glu | Ala | Ser | Leu | Gln | Glu | Leu | Lys | Ala | Ser | Pro | Arg | |
| | | 195 | | | | | 200 | | | | | 205 | | | | |
| ATG | GTG | CCC | CGT | GCT | GTG | TAC | CTG | CCC | AAT | TGT | GAC | CGC | AAA | GGA | TTC | 728 |
| Met | Val | Pro | Arg | Ala | Val | Tyr | Leu | Pro | Asn | Cys | Asp | Arg | Lys | Gly | Phe | |
| | 210 | | | | | 215 | | | | | 220 | | | | | |
| TAC | AAG | AGA | AAG | CAG | TGC | AAA | CCT | TCC | CGT | GGC | CGC | AAG | CGT | GGC | ATC | 776 |
| Tyr | Lys | Arg | Lys | Gln | Cys | Lys | Pro | Ser | Arg | Gly | Arg | Lys | Arg | Gly | Ile | |
| 225 | | | | | 230 | | | | | 235 | | | | | 240 | |
| TGC | TGG | TGC | GTG | GAC | AAG | TAC | GGG | ATG | AAG | CTG | CCA | GGC | ATG | GAG | TAC | 824 |
| Cys | Trp | Cys | Val | Asp | Lys | Tyr | Gly | Met | Lys | Leu | Pro | Gly | Met | Glu | Tyr | |
| | | | | 245 | | | | | 250 | | | | | 255 | | |
| GTT | GAC | GGG | GAC | TTT | CAG | TGC | CAC | ACC | TTC | GAC | AGC | AGC | AAC | GTT | GAG | 872 |
| Val | Asp | Gly | Asp | Phe | Gln | Cys | His | Thr | Phe | Asp | Ser | Ser | Asn | Val | Glu | |
| | | | 260 | | | | | 265 | | | | | 270 | | | |
| TGATGCGTCC | | CCCCCAACC | | TTTCCCTCAC | | CCCCTCCCAC | | CCCCAGCCCC | | GACTCCAGCC | | | | | | 932 |
| AGCGCCTCCC | | TCCACCCCAG | | GACGCCACTC | | ATTTCATCTC | | ATTTAAGGGA | | AAAATATATA | | | | | | 992 |
| TCTATCTATT | | TGAAAAAAAA | | AAAAAAAACC | | C | | | | | | | | | | 1023 |

( 2 ) INFORMATION FOR SEQ ID NO:8:

( i ) SEQUENCE CHARACTERISTICS:
( A ) LENGTH: 272 amino acids
( B ) TYPE: amino acid -continued (D) TOPOLOGY: linear (ii) MOLECULE TYPE: protein (xi) SEQUENCE DESCRIPTION: SEQ ID NO:8:

| Met | Val | Leu | Leu | Thr | Ala | Val | Leu | Leu | Leu | Ala | Ala | Tyr | Ala | Gly |
|---|---|---|---|---|---|---|---|---|---|---|---|---|---|---|
| 1 | | | | 5 | | | | | 10 | | | | | 15 |

| Pro | Ala | Gln | Ser | Leu | Gly | Ser | Phe | Val | His | Cys | Glu | Pro | Cys | Asp | Glu |
|---|---|---|---|---|---|---|---|---|---|---|---|---|---|---|---|
| | | | 20 | | | | | 25 | | | | | 30 | | |

| Lys | Ala | Leu | Ser | Met | Cys | Pro | Pro | Ser | Pro | Leu | Gly | Cys | Glu | Leu | Val |
|---|---|---|---|---|---|---|---|---|---|---|---|---|---|---|---|
| | | | 35 | | | | 40 | | | | | 45 | | | |

| Lys | Glu | Pro | Gly | Cys | Gly | Cys | Cys | Met | Thr | Cys | Ala | Leu | Ala | Glu | Gly |
|---|---|---|---|---|---|---|---|---|---|---|---|---|---|---|---|
| | 50 | | | | | 55 | | | | | 60 | | | | |

| Gln | Ser | Cys | Gly | Val | Tyr | Thr | Glu | Arg | Cys | Ala | Gln | Gly | Leu | Arg | Cys |
|---|---|---|---|---|---|---|---|---|---|---|---|---|---|---|---|
| 65 | | | | | 70 | | | | | 75 | | | | | 80 |

| Leu | Pro | Arg | Gln | Asp | Glu | Glu | Lys | Pro | Leu | His | Ala | Leu | Leu | His | Gly |
|---|---|---|---|---|---|---|---|---|---|---|---|---|---|---|---|
| | | | | 85 | | | | | 90 | | | | | 95 | |

| Arg | Gly | Val | Cys | Leu | Asn | Glu | Lys | Ser | Tyr | Arg | Glu | Gln | Val | Lys | Ile |
|---|---|---|---|---|---|---|---|---|---|---|---|---|---|---|---|
| | | | 100 | | | | | 105 | | | | | 110 | | |

| Glu | Arg | Asp | Ser | Arg | Glu | His | Glu | Glu | Pro | Thr | Thr | Ser | Glu | Met | Ala |
|---|---|---|---|---|---|---|---|---|---|---|---|---|---|---|---|
| | | | 115 | | | | | 120 | | | | | 125 | | |

| Glu | Glu | Thr | Tyr | Ser | Pro | Lys | Ile | Phe | Arg | Pro | Lys | His | Thr | Arg | Ile |
|---|---|---|---|---|---|---|---|---|---|---|---|---|---|---|---|
| | 130 | | | | | 135 | | | | | 140 | | | | |

| Ser | Glu | Leu | Lys | Ala | Glu | Ala | Val | Lys | Lys | Asp | Arg | Arg | Lys | Lys | Leu |
|---|---|---|---|---|---|---|---|---|---|---|---|---|---|---|---|
| 145 | | | | | 150 | | | | | 155 | | | | | 160 |

| Thr | Gln | Ser | Lys | Phe | Val | Gly | Gly | Ala | Glu | Asn | Thr | Ala | His | Pro | Arg |
|---|---|---|---|---|---|---|---|---|---|---|---|---|---|---|---|
| | | | | 165 | | | | | 170 | | | | | 175 | |

| Ile | Ile | Ser | Ala | Pro | Glu | Met | Arg | Gln | Glu | Ser | Glu | Gln | Gly | Pro | Cys |
|---|---|---|---|---|---|---|---|---|---|---|---|---|---|---|---|
| | | | 180 | | | | | 185 | | | | | 190 | | |

| Arg | Arg | His | Met | Glu | Ala | Ser | Leu | Gln | Glu | Leu | Lys | Ala | Ser | Pro | Arg |
|---|---|---|---|---|---|---|---|---|---|---|---|---|---|---|---|
| | | 195 | | | | | 200 | | | | | 205 | | | |

| Met | Val | Pro | Arg | Ala | Val | Tyr | Leu | Pro | Asn | Cys | Asp | Arg | Lys | Gly | Phe |
|---|---|---|---|---|---|---|---|---|---|---|---|---|---|---|---|
| | 210 | | | | | 215 | | | | | 220 | | | | |

| Tyr | Lys | Arg | Lys | Gln | Cys | Lys | Pro | Ser | Arg | Gly | Arg | Lys | Arg | Gly | Ile |
|---|---|---|---|---|---|---|---|---|---|---|---|---|---|---|---|
| 225 | | | | | 230 | | | | | 235 | | | | | 240 |

| Cys | Trp | Cys | Val | Asp | Lys | Tyr | Gly | Met | Lys | Leu | Pro | Gly | Met | Glu | Tyr |
|---|---|---|---|---|---|---|---|---|---|---|---|---|---|---|---|
| | | | | 245 | | | | | 250 | | | | | 255 | |

| Val | Asp | Gly | Asp | Phe | Gln | Cys | His | Thr | Phe | Asp | Ser | Ser | Asn | Val | Glu |
|---|---|---|---|---|---|---|---|---|---|---|---|---|---|---|---|
| | | | 260 | | | | | 265 | | | | | 270 | | |

(2) INFORMATION FOR SEQ ID NO:9:

(i) SEQUENCE CHARACTERISTICS:
    (A) LENGTH: 1694 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (ix) FEATURE:
    (A) NAME/KEY: CDS
    (B) LOCATION: 2..931

(xi) SEQUENCE DESCRIPTION: SEQ ID NO:9:

| C | TCT | CTC | AAG | GCC | AAC | ATC | CCT | GAG | GTG | GAA | GCT | GTC | CTC | AAC | ACC | 46 |
|---|---|---|---|---|---|---|---|---|---|---|---|---|---|---|---|---|
| | Ser | Leu | Lys | Ala | Asn | Ile | Pro | Glu | Val | Glu | Ala | Val | Leu | Asn | Thr | |
| | 1 | | | | 5 | | | | | 10 | | | | | 15 | |

```
GAC AGG AGT TTG GTG TGT GAT GGG AAG AGG GGC TTA TTA ACT CGT CTG         94
Asp Arg Ser Leu Val Cys Asp Gly Lys Arg Gly Leu Leu Thr Arg Leu
                 20              25                  30

CTG CAG GTC ATG AAG AAG GAG CCA GCA GAG TCG TCT TTC AGG TTT TGG        142
Leu Gln Val Met Lys Lys Glu Pro Ala Glu Ser Ser Phe Arg Phe Trp
             35              40                  45

CAA GCT CGG GCT GTG GAG AGT TTC CTC CGA GGG ACC ACC TCC TAT GCA        190
Gln Ala Arg Ala Val Glu Ser Phe Leu Arg Gly Thr Thr Ser Tyr Ala
         50              55                  60

GAC CAG ATG TTC CTG CTG AAG CGA GGC CTC TTG GAG CAC ATC CTT TAC        238
Asp Gln Met Phe Leu Leu Lys Arg Gly Leu Leu Glu His Ile Leu Tyr
     65              70                  75

TGC ATT GTG GAC AGC GAG TGT AAG TCA AGG GAT GTG CTC CAG AGT TAC        286
Cys Ile Val Asp Ser Glu Cys Lys Ser Arg Asp Val Leu Gln Ser Tyr
 80              85                  90                       95

TTT GAC CTC CTG GGG GAG CTG ATG AAG TTC AAC GTT GAT GCA TTC AAG        334
Phe Asp Leu Leu Gly Glu Leu Met Lys Phe Asn Val Asp Ala Phe Lys
             100                 105                 110

AGA TTC AAT AAA TAT ATC AAC ACC GAT GCA AAG TTC CAG GTA TTC CTG        382
Arg Phe Asn Lys Tyr Ile Asn Thr Asp Ala Lys Phe Gln Val Phe Leu
             115                 120                 125

AAG CAG ATC AAC AGC TCC CTG GTG GAC TCC AAC ATG CTG GTG CGC TGT        430
Lys Gln Ile Asn Ser Ser Leu Val Asp Ser Asn Met Leu Val Arg Cys
             130                 135                 140

GTC ACT CTG TCC CTG GAC CGA TTT GAA AAC CAG GTG GAT ATG AAA GTT        478
Val Thr Leu Ser Leu Asp Arg Phe Glu Asn Gln Val Asp Met Lys Val
     145                 150                 155

GCC GAG GTA CTG TCT GAA TGC CGC CTG CTC GCC TAC ATA TCC CAG GTG        526
Ala Glu Val Leu Ser Glu Cys Arg Leu Leu Ala Tyr Ile Ser Gln Val
160             165                 170                 175

CCC ACG CAG ATG TCC TTC CTC TTC CGC CTC ATC AAC ATC ATC CAC GTG        574
Pro Thr Gln Met Ser Phe Leu Phe Arg Leu Ile Asn Ile Ile His Val
             180                 185                 190

CAG ACG CTG ACC CAG GAG AAC GTC AGC TGC CTC AAC ACC AGC CTG GTG        622
Gln Thr Leu Thr Gln Glu Asn Val Ser Cys Leu Asn Thr Ser Leu Val
         195                 200                 205

ATC CTG ATG CTG GCC CGA CGG AAA GAG CGG CTG CCC CTG TAC CTG CGG        670
Ile Leu Met Leu Ala Arg Arg Lys Glu Arg Leu Pro Leu Tyr Leu Arg
         210                 215                 220

CTG CTG CAG CGG ATG GAG CAC AGC AAG AAG TAC CCC GGC TTC CTG CTC        718
Leu Leu Gln Arg Met Glu His Ser Lys Lys Tyr Pro Gly Phe Leu Leu
     225                 230                 235

AAC AAC TTC CAC AAC CTG CTG CGC TTC TGG CAG CAG CAC TAC CTG CAC        766
Asn Asn Phe His Asn Leu Leu Arg Phe Trp Gln Gln His Tyr Leu His
240             245                 250                 255

AAG GAC AAG GAC AGC ACC TGC CTA GAG AAC AGC TCC TGC ATC AGC TTC        814
Lys Asp Lys Asp Ser Thr Cys Leu Glu Asn Ser Ser Cys Ile Ser Phe
             260                 265                 270

TCA TAC TGG AAG GAG ACA GTG TCC ATC CTG TTG AAC CCG GAC CGG CAG        862
Ser Tyr Trp Lys Glu Thr Val Ser Ile Leu Leu Asn Pro Asp Arg Gln
         275                 280                 285

TCA CCC TCT GCT CTC GTT AGC TAC ATT GAG GAG CCC TAC ATG GAC ATA        910
Ser Pro Ser Ala Leu Val Ser Tyr Ile Glu Glu Pro Tyr Met Asp Ile
     290                 295                 300

GAC AGG GAC TTC ACT GAG GAG TGACCTTGGG CCAGGCCTCG GAGGCTGCT            961
Asp Arg Asp Phe Thr Glu Glu
     305                 310

GGGCCAGTGT GGGTGAGCGT GGGTACGATG CCACACGCCC TGCCCTGTTC CCGTTCCTCC     1021

CTGCTGCTCT CTGCCTGCCC CAGGTCTTTG GGTACAGGCT TGGTGGGAGG GAAGTCCTAG     1081
```

```
AAGCCCTTGG  TCCCCCTGGG  TCTGAGGGCC  CTAGGTCATG  GAGAGCCTCA  GTCCCCATAA  1141

TGAGGACAGG  GTACCATGCC  CACCTTTCCT  TCAGAACCCT  GGGGCCCAGG  GCCACCCAGA  1201

GGTAAGAGGA  CATTTAGCAT  TAGCTCTGTG  TGAGCTCCTG  CCGGTTTCTT  GGCTGTCAGT  1261

CAGTCCCAGA  GTGGGGAGGA  AGATATGGGT  GACCCCCACC  CCCCATCTGT  GAGCCAAGCC  1321

TCCCTTGTCC  CTGGCCTTTG  GACCCAGGCA  AAGGCTTCTG  AGCCCTGGGC  AGGGGTGGTG  1381

GGTACCAGAG  AATGCTGCCT  TCCCCAAGC   CTGCCCCTCT  GCCTCATTTT  CCTGTAGCTC  1441

CTCTGGTTCT  GTTTGCTCAT  TGGCCGCTGT  GTTCATCCAA  GGGGGTTCTC  CCAGAAGTGA  1501

GGGGCCTTTC  CCTCCATCCC  TTGGGGCACG  GGGCAGCTGT  GCCTGCCCTG  CCTCTGCCTG  1561

AGGCAGCCGC  TCCTGCCTGA  GCCTGGACAT  GGGGCCCTTC  CTTGTGTTGC  CAATTTATTA  1621

ACAGCAAATA  AACCAATTAA  ATGGAGACTA  TTAAATAACT  TTATTTAAA   AATGAAAAAA  1681

AAAAAAAAAA  AAA                                                         1694
```

( 2 ) INFORMATION FOR SEQ ID NO:10:

( i ) SEQUENCE CHARACTERISTICS:
        ( A ) LENGTH: 310 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser Leu Lys Ala Asn Ile Pro Glu Val Glu Ala Val Leu Asn Thr Asp
 1               5                  10                  15

Arg Ser Leu Val Cys Asp Gly Lys Arg Gly Leu Leu Thr Arg Leu Leu
                20                  25                  30

Gln Val Met Lys Lys Glu Pro Ala Glu Ser Ser Phe Arg Phe Trp Gln
            35                  40                  45

Ala Arg Ala Val Glu Ser Phe Leu Arg Gly Thr Thr Ser Tyr Ala Asp
        50                  55                  60

Gln Met Phe Leu Leu Lys Arg Gly Leu Leu Glu His Ile Leu Tyr Cys
65                  70                  75                  80

Ile Val Asp Ser Glu Cys Lys Ser Arg Asp Val Leu Gln Ser Tyr Phe
                85                  90                  95

Asp Leu Leu Gly Glu Leu Met Lys Phe Asn Val Asp Ala Phe Lys Arg
                100                 105                 110

Phe Asn Lys Tyr Ile Asn Thr Asp Ala Lys Phe Gln Val Phe Leu Lys
            115                 120                 125

Gln Ile Asn Ser Ser Leu Val Asp Ser Asn Met Leu Val Arg Cys Val
        130                 135                 140

Thr Leu Ser Leu Asp Arg Phe Glu Asn Gln Val Asp Met Lys Val Ala
145                 150                 155                 160

Glu Val Leu Ser Glu Cys Arg Leu Leu Ala Tyr Ile Ser Gln Val Pro
                165                 170                 175

Thr Gln Met Ser Phe Leu Phe Arg Leu Ile Asn Ile Ile His Val Gln
            180                 185                 190

Thr Leu Thr Gln Glu Asn Val Ser Cys Leu Asn Thr Ser Leu Val Ile
        195                 200                 205

Leu Met Leu Ala Arg Arg Lys Glu Arg Leu Pro Leu Tyr Leu Arg Leu
        210                 215                 220

Leu Gln Arg Met Glu His Ser Lys Lys Tyr Pro Gly Phe Leu Leu Asn
225                 230                 235                 240

Asn Phe His Asn Leu Leu Arg Phe Trp Gln Gln His Tyr Leu His Lys
```

```
                              245                         250                         255
    Asp  Lys  Asp  Ser  Thr  Cys  Leu  Glu  Asn  Ser  Ser  Cys  Ile  Ser  Phe  Ser
                   260                         265                    270

Tyr  Trp  Lys  Glu  Thr  Val  Ser  Ile  Leu  Leu  Asn  Pro  Asp  Arg  Gln  Ser
              275                         280                    285

Pro  Ser  Ala  Leu  Val  Ser  Tyr  Ile  Glu  Glu  Pro  Tyr  Met  Asp  Ile  Asp
         290                         295                    300

Arg  Asp  Phe  Thr  Glu  Glu
    305                     310
```

( 2 ) INFORMATION FOR SEQ ID NO:11:

( i ) SEQUENCE CHARACTERISTICS:
        ( A ) LENGTH: 2735 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..1822

( x i ) SEQUENCE DESCRIPTION: SEQ ID NO:11:

```
G  GAG  ATC  AGT  CGG  AAG  GTG  TAC  AAG  GGA  ATG  TTA  GAC  CTC  CTC  AAG        46
   Glu  Ile  Ser  Arg  Lys  Val  Tyr  Lys  Gly  Met  Leu  Asp  Leu  Leu  Lys
    1              5                        10                      15

TGT  ACA  GTC  CTC  AGC  TTG  GAG  CAG  TCC  TAT  GCC  CAC  GCG  GGT  CTG  GGT      94
Cys  Thr  Val  Leu  Ser  Leu  Glu  Gln  Ser  Tyr  Ala  His  Ala  Gly  Leu  Gly
                    20                       25                      30

GGC  ATG  GCC  AGC  ATC  TTT  GGG  CTT  TTG  GAG  ATT  GCC  CAG  ACC  CAC  TAC     142
Gly  Met  Ala  Ser  Ile  Phe  Gly  Leu  Leu  Glu  Ile  Ala  Gln  Thr  His  Tyr
               35                       40                       45

TAT  AGT  AAA  GAA  CCA  GAC  AAG  CGG  AAG  AGA  AGT  CCA  ACA  GAA  AGT  GTA     190
Tyr  Ser  Lys  Glu  Pro  Asp  Lys  Arg  Lys  Arg  Ser  Pro  Thr  Glu  Ser  Val
          50                       55                       60

AAT  ACC  CCA  GTT  GGC  AAG  GAT  CCT  GGC  CTA  GCT  GGG  CGG  GGG  GAC  CCA     238
Asn  Thr  Pro  Val  Gly  Lys  Asp  Pro  Gly  Leu  Ala  Gly  Arg  Gly  Asp  Pro
     65                       70                       75

AAG  GCT  ATG  GCA  CAA  CTG  AGA  GTT  CCA  CAA  CTG  GGA  CCT  CGG  GCA  CCA     286
Lys  Ala  Met  Ala  Gln  Leu  Arg  Val  Pro  Gln  Leu  Gly  Pro  Arg  Ala  Pro
80                       85                       90                       95

AGT  GCC  ACA  GGA  AAG  GGT  CCT  AAG  GAA  CTG  GAC  ACC  AGA  AGT  TTA  AAG     334
Ser  Ala  Thr  Gly  Lys  Gly  Pro  Lys  Glu  Leu  Asp  Thr  Arg  Ser  Leu  Lys
                    100                      105                     110

GAA  GAA  AAT  TTT  ATA  GCA  TCT  ATT  GGG  CCT  GAA  GTA  ATC  AAA  CCT  GTC     382
Glu  Glu  Asn  Phe  Ile  Ala  Ser  Ile  Gly  Pro  Glu  Val  Ile  Lys  Pro  Val
               115                      120                     125

TTT  GAC  CTT  GGT  GAG  ACA  GAG  GAG  AAA  AAG  TCC  CAG  ATC  AGC  GCA  GAC     430
Phe  Asp  Leu  Gly  Glu  Thr  Glu  Glu  Lys  Lys  Ser  Gln  Ile  Ser  Ala  Asp
          130                      135                     140

AGT  GGT  GTG  AGC  CTG  ACG  TCT  AGT  TCC  CAG  AGG  ACT  GAT  CAA  GAC  TCT     478
Ser  Gly  Val  Ser  Leu  Thr  Ser  Ser  Ser  Gln  Arg  Thr  Asp  Gln  Asp  Ser
     145                      150                     155

GTC  ATC  GGC  GTG  AGT  CCA  GCT  GTT  ATG  ATC  CGC  AGC  TCA  AGT  CAG  GAT     526
Val  Ile  Gly  Val  Ser  Pro  Ala  Val  Met  Ile  Arg  Ser  Ser  Ser  Gln  Asp
160                      165                     170                     175

TCT  GAA  GTT  AGC  ACC  GTG  GTG  AGT  AAT  AGC  TCT  GGA  GAG  ACC  CTT  GGA     574
Ser  Glu  Val  Ser  Thr  Val  Val  Ser  Asn  Ser  Ser  Gly  Glu  Thr  Leu  Gly
                    180                      185                     190
```

| | | | | | | | | | | | | | | | |
|---|---|---|---|---|---|---|---|---|---|---|---|---|---|---|---|
| GCT | GAC | AGT | GAC | TTG | AGC | AGC | AAT | GCA | GGT | GAT | GGA | CCA | GGT | GGC | GAG | 622 |
| Ala | Asp | Ser | Asp<br>195 | Leu | Ser | Ser | Asn | Ala<br>200 | Gly | Asp | Gly | Pro | Gly<br>205 | Gly | Glu |

```
GCT  GAC  AGT  GAC  TTG  AGC  AGC  AAT  GCA  GGT  GAT  GGA  CCA  GGT  GGC  GAG       622
Ala  Asp  Ser  Asp  Leu  Ser  Ser  Asn  Ala  Gly  Asp  Gly  Pro  Gly  Gly  Glu
               195                      200                      205

GGC  AGT  GTT  CAC  CTG  GCA  AGC  TCT  CGG  GGC  ACT  TTG  TCT  GAT  AGT  GAA       670
Gly  Ser  Val  His  Leu  Ala  Ser  Ser  Arg  Gly  Thr  Leu  Ser  Asp  Ser  Glu
               210                      215                      220

ATT  GAG  ACC  AAC  TCT  GCC  ACA  AGC  ACC  ATC  TTT  GGT  AAA  GCC  CAC  AGC       718
Ile  Glu  Thr  Asn  Ser  Ala  Thr  Ser  Thr  Ile  Phe  Gly  Lys  Ala  His  Ser
               225                      230                      235

TTG  AAG  CCA  AGC  ATA  AAG  GAG  AAG  CTG  GCA  GGC  AGC  CCC  ATT  CGT  ACT       766
Leu  Lys  Pro  Ser  Ile  Lys  Glu  Lys  Leu  Ala  Gly  Ser  Pro  Ile  Arg  Thr
240                      245                      250                      255

TCT  GAA  GAT  GTG  AGC  CAG  CGA  GTC  TAT  CTC  TAT  GAG  GGA  CTC  CTA  GGC       814
Ser  Glu  Asp  Val  Ser  Gln  Arg  Val  Tyr  Leu  Tyr  Glu  Gly  Leu  Leu  Gly
               260                      265                      270

AAA  GAG  CGT  TCT  ACT  TTA  TGG  GAC  CAA  ATG  CAA  TTC  TGG  GAA  GAT  GCC       862
Lys  Glu  Arg  Ser  Thr  Leu  Trp  Asp  Gln  Met  Gln  Phe  Trp  Glu  Asp  Ala
               275                      280                      285

TTC  TTA  GAT  GCT  GTG  ATG  TTG  GAG  AGA  GAA  GGG  ATG  GGT  ATG  GAC  CAG       910
Phe  Leu  Asp  Ala  Val  Met  Leu  Glu  Arg  Glu  Gly  Met  Gly  Met  Asp  Gln
               290                      295                      300

GGT  CCC  CAG  GAA  ATG  ATC  GAC  AGG  TAC  CTG  TCC  CTT  GGA  GAA  CAT  GAC       958
Gly  Pro  Gln  Glu  Met  Ile  Asp  Arg  Tyr  Leu  Ser  Leu  Gly  Glu  His  Asp
     305                      310                      315

CGG  AAG  CGC  CTG  GAA  GAT  GAT  GAA  GAT  CGC  TTG  CTG  GCC  ACA  CTT  CTG      1006
Arg  Lys  Arg  Leu  Glu  Asp  Asp  Glu  Asp  Arg  Leu  Leu  Ala  Thr  Leu  Leu
320                      325                      330                      335

CAC  AAC  CTC  ATC  TCC  TAC  ATG  CTG  CTG  ATG  AAG  GTA  AAT  AAG  AAT  GAC      1054
His  Asn  Leu  Ile  Ser  Tyr  Met  Leu  Leu  Met  Lys  Val  Asn  Lys  Asn  Asp
               340                      345                      350

ATC  CGC  AAG  AAG  GTG  AGG  CGC  CTA  ATG  GGA  AAG  TCG  CAC  ATT  GGG  CTT      1102
Ile  Arg  Lys  Lys  Val  Arg  Arg  Leu  Met  Gly  Lys  Ser  His  Ile  Gly  Leu
               355                      360                      365

GTG  TAC  AGC  CAG  CAA  ATC  AAT  GAG  GTG  CTT  GAT  CAG  CTG  GCG  AAC  CTG      1150
Val  Tyr  Ser  Gln  Gln  Ile  Asn  Glu  Val  Leu  Asp  Gln  Leu  Ala  Asn  Leu
               370                      375                      380

AAT  GGA  CGC  GAT  CTC  TCT  ATC  TGG  TCC  AGT  GGC  AGC  CGG  CAC  ATG  AAG      1198
Asn  Gly  Arg  Asp  Leu  Ser  Ile  Trp  Ser  Ser  Gly  Ser  Arg  His  Met  Lys
     385                      390                      395

AAG  CAG  ACA  TTT  GTG  GTA  CAT  GCA  GGG  ACA  GAT  ACA  AAC  GGA  GAT  ATC      1246
Lys  Gln  Thr  Phe  Val  Val  His  Ala  Gly  Thr  Asp  Thr  Asn  Gly  Asp  Ile
400                      405                      410                      415

TTT  TTC  ATG  GAG  GTG  TGC  GAT  GAC  TGT  GTG  GTG  TTG  CGT  AGT  AAC  ATC      1294
Phe  Phe  Met  Glu  Val  Cys  Asp  Asp  Cys  Val  Val  Leu  Arg  Ser  Asn  Ile
               420                      425                      430

GGA  ACA  GTG  TAT  GAG  CGC  TGG  TGG  TAC  GAG  AAG  CTC  ATC  AAC  ATG  ACC      1342
Gly  Thr  Val  Tyr  Glu  Arg  Trp  Trp  Tyr  Glu  Lys  Leu  Ile  Asn  Met  Thr
               435                      440                      445

TAC  TGT  CCC  AAG  ACG  AAG  GTG  TTG  TGC  TTG  TGG  CGT  AGA  AAT  GGC  TCT      1390
Tyr  Cys  Pro  Lys  Thr  Lys  Val  Leu  Cys  Leu  Trp  Arg  Arg  Asn  Gly  Ser
          450                      455                      460

GAG  ACC  CAG  CTC  AAC  AAG  TTC  TAT  ACT  AAA  AAG  TGT  CGG  GAG  CTG  TAC      1438
Glu  Thr  Gln  Leu  Asn  Lys  Phe  Tyr  Thr  Lys  Lys  Cys  Arg  Glu  Leu  Tyr
     465                      470                      475

TAC  TGT  GTG  AAG  GAC  AGC  ATG  GAG  CGC  GCT  GCC  GCC  CGA  CAG  CAA  AGC      1486
Tyr  Cys  Val  Lys  Asp  Ser  Met  Glu  Arg  Ala  Ala  Ala  Arg  Gln  Gln  Ser
480                      485                      490                      495

ATC  AAA  CCC  GGA  CCT  GAA  TTG  GGT  GGC  GAG  TTC  CCT  GTG  CAG  GAC  CTG      1534
Ile  Lys  Pro  Gly  Pro  Glu  Leu  Gly  Gly  Glu  Phe  Pro  Val  Gln  Asp  Leu
               500                      505                      510
```

| | | | | | | | | | | | | | | | | |
|---|---|---|---|---|---|---|---|---|---|---|---|---|---|---|---|---|
|AAG|ACT|GGT|GAG|GGT|GGC|CTG|CTG|CAG|GTG|ACC|CTG|GAA|GGG|ATC|AAC|1582|
|Lys|Thr|Gly|Glu|Gly|Gly|Leu|Leu|Gln|Val|Thr|Leu|Glu|Gly|Ile|Asn| |
| | | |515| | | | |520| | | | |525| | | |
|CTC|AAA|TTC|ATG|CAC|AAT|CAG|GTT|TTC|ATA|GAG|CTG|AAT|CAC|ATT|AAA|1630|
|Leu|Lys|Phe|Met|His|Asn|Gln|Val|Phe|Ile|Glu|Leu|Asn|His|Ile|Lys| |
| | |530| | | | |535| | | | |540| | | | |
|AAG|TGC|AAT|ACA|GTT|CGA|GGC|GTC|TTT|GTC|CTG|GAG|GAA|TTT|GTT|CCT|1678|
|Lys|Cys|Asn|Thr|Val|Arg|Gly|Val|Phe|Val|Leu|Glu|Glu|Phe|Val|Pro| |
| |545| | | | |550| | | | |555| | | | | |
|GAA|ATT|AAA|GAA|GTG|GTG|AGC|CAC|AAG|TAC|AAG|ACA|CCA|ATG|GCC|CAC|1726|
|Glu|Ile|Lys|Glu|Val|Val|Ser|His|Lys|Tyr|Lys|Thr|Pro|Met|Ala|His| |
|560| | | | |565| | | | |570| | | | |575| |
|GAA|ATC|TGC|TAC|TCC|GTA|TTA|TGT|CTC|TTC|TCG|TAC|GTG|GCT|GCA|GTT|1774|
|Glu|Ile|Cys|Tyr|Ser|Val|Leu|Cys|Leu|Phe|Ser|Tyr|Val|Ala|Ala|Val| |
| | | | |580| | | | |585| | | | |590| | |
|CAT|AGC|AGT|GAG|GAA|GAT|CTC|AGA|ACC|CCG|CCC|CGG|CCT|GTC|TCT|AGC|1822|
|His|Ser|Ser|Glu|Glu|Asp|Leu|Arg|Thr|Pro|Pro|Arg|Pro|Val|Ser|Ser| |
| | | |595| | | | |600| | | | |605| | | |

| | | | | |
|---|---|---|---|---|
|TGATGGAGAG|GGGCTACGCA|GCTGCCCCAG|CCCAGGGCAC|GCCCCTGGCC CCTTGCTGTT|1882|
|CCCAAGTGCA|CGATGCTGCT|GTGACTGAGG|AGTGGATGAT|GCTCGTGTGT CCTCTGCAAG|1942|
|CCCCCTGCTG|TGGCTTGGTT|GGTTACCGGT|TATGTGTCCC|TCTGAGTGTG TCTTGAGCGT|2002|
|GTCCACCTTC|TCCCTCTCCA|CTCCCAGAAG|ACCAAACTGC|CTTCCCCTCA GGGCTCAAGA|2062|
|ATGTGTACAG|TCTGTGGGGC|CGGTGTGAAC|CCACTATTTT|GTGTCCTTGA GACATTTGTG|2122|
|TTGTGGTTCC|TTGTCCTTGT|CCCTGGCGTT|ATAACTGTCC|ACTGCAAGAG TCTGGCTCTC|2182|
|CCTTCTCTGT|GACCCGGCAT|GACTGGGCGC|CTGGAGCAGT|TTCACTCTGT GAGGAGTGAG|2242|
|GGAACCCTGG|GGCTCACCCT|CTCAGAGGAA|GGGCACAGAG|AGGAAGGGAA GAATTGGGGG|2302|
|GCAGCCGGAG|TGAGTGGCAG|CCTCCCTGCT|TCCTTCTGCA|TTCCCAAGCC GGCAGCTACT|2362|
|GCCCAGGGCC|CGCAGTGTTG|GCTGCTGCCT|GCCACAGCCT|CTGTGACTGC AGTGGAGCGG|2422|
|CGAATTCCCT|GTGGCCTGCC|ACGCCTTCGG|CATCAGAGGA|TGGAGTGGTC GAGGCTAGTG|2482|
|GAGTCCCAGG|GACCGCTGGC|TGCTCTGCCT|GAGCATCAGG|GAGGGGCAG GAAAGACCAA|2542|
|GCTGGGTTTG|CACATCTGTC|TGCAGGCTGT|CTCTCCAGGC|ACGGGGTGTC AGGAGGGAGA|2602|
|GACAGCCTGG|GTATGGGCAA|GAAATGACTG|TAAATATTTC|AGCCCCACAT TATTTATAGA|2662|
|AAATGTACAG|TTGTGTGAAT|GTGAAATAAA|TGTCCTCAAC|TCCCAAAAAA AAAAAAAAA|2722|
|AAAAAAAAAA AAA| | | | |2735|

( 2 ) INFORMATION FOR SEQ ID NO:12:

( i ) SEQUENCE CHARACTERISTICS:
        ( A ) LENGTH: 607 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
|Glu|Ile|Ser|Arg|Lys|Val|Tyr|Lys|Gly|Met|Leu|Asp|Leu|Leu|Lys|Cys|
|1| | | |5| | | | |10| | | | |15| |
|Thr|Val|Leu|Ser|Leu|Glu|Gln|Ser|Tyr|Ala|His|Ala|Gly|Leu|Gly|Gly|
| | | | |20| | | | |25| | | | |30| |
|Met|Ala|Ser|Ile|Phe|Gly|Leu|Leu|Glu|Ile|Ala|Gln|Thr|His|Tyr|Tyr|
| | | |35| | | | |40| | | | |45| | |
|Ser|Lys|Glu|Pro|Asp|Lys|Arg|Lys|Arg|Ser|Pro|Thr|Glu|Ser|Val|Asn|
| |50| | | | |55| | | | |60| | | | |

| | | | | | | | | | | | | | | | |
|---|---|---|---|---|---|---|---|---|---|---|---|---|---|---|---|
| Thr | Pro | Val | Gly | Lys | Asp | Pro | Gly | Leu | Ala | Gly | Arg | Gly | Asp | Pro | Lys |
| 65 | | | | 70 | | | | 75 | | | | | | | 80 |
| Ala | Met | Ala | Gln | Leu | Arg | Val | Pro | Gln | Leu | Gly | Pro | Arg | Ala | Pro | Ser |
| | | | 85 | | | | | 90 | | | | | 95 | | |
| Ala | Thr | Gly | Lys | Gly | Pro | Lys | Glu | Leu | Asp | Thr | Arg | Ser | Leu | Lys | Glu |
| | | | 100 | | | | 105 | | | | | 110 | | | |
| Glu | Asn | Phe | Ile | Ala | Ser | Ile | Gly | Pro | Glu | Val | Ile | Lys | Pro | Val | Phe |
| | | 115 | | | | | 120 | | | | | 125 | | | |
| Asp | Leu | Gly | Glu | Thr | Glu | Lys | Lys | Ser | Gln | Ile | Ser | Ala | Asp | Ser | |
| | 130 | | | | | 135 | | | | 140 | | | | | |
| Gly | Val | Ser | Leu | Thr | Ser | Ser | Gln | Arg | Thr | Asp | Gln | Asp | Ser | Val | |
| 145 | | | | | 150 | | | | 155 | | | | | 160 | |
| Ile | Gly | Val | Ser | Pro | Ala | Val | Met | Ile | Arg | Ser | Ser | Ser | Gln | Asp | Ser |
| | | | | 165 | | | | | 170 | | | | | 175 | |
| Glu | Val | Ser | Thr | Val | Val | Ser | Asn | Ser | Ser | Gly | Glu | Thr | Leu | Gly | Ala |
| | | | 180 | | | | | 185 | | | | | 190 | | |
| Asp | Ser | Asp | Leu | Ser | Ser | Asn | Ala | Gly | Asp | Gly | Pro | Gly | Gly | Glu | Gly |
| | | 195 | | | | | 200 | | | | | 205 | | | |
| Ser | Val | His | Leu | Ala | Ser | Ser | Arg | Gly | Thr | Leu | Ser | Asp | Ser | Glu | Ile |
| | 210 | | | | | 215 | | | | | 220 | | | | |
| Glu | Thr | Asn | Ser | Ala | Thr | Ser | Thr | Ile | Phe | Gly | Lys | Ala | His | Ser | Leu |
| 225 | | | | | 230 | | | | | 235 | | | | | 240 |
| Lys | Pro | Ser | Ile | Lys | Glu | Lys | Leu | Ala | Gly | Ser | Pro | Ile | Arg | Thr | Ser |
| | | | | 245 | | | | | 250 | | | | | 255 | |
| Glu | Asp | Val | Ser | Gln | Arg | Val | Tyr | Leu | Tyr | Glu | Gly | Leu | Leu | Gly | Lys |
| | | | 260 | | | | 265 | | | | | 270 | | | |
| Glu | Arg | Ser | Thr | Leu | Trp | Asp | Gln | Met | Gln | Phe | Trp | Glu | Asp | Ala | Phe |
| | | 275 | | | | | 280 | | | | | 285 | | | |
| Leu | Asp | Ala | Val | Met | Leu | Glu | Arg | Glu | Gly | Met | Gly | Met | Asp | Gln | Gly |
| | | 290 | | | | | 295 | | | | | 300 | | | |
| Pro | Gln | Glu | Met | Ile | Asp | Arg | Tyr | Leu | Ser | Leu | Gly | Glu | His | Asp | Arg |
| 305 | | | | | 310 | | | | | 315 | | | | | 320 |
| Lys | Arg | Leu | Glu | Asp | Asp | Glu | Asp | Arg | Leu | Leu | Ala | Thr | Leu | Leu | His |
| | | | | 325 | | | | | 330 | | | | | 335 | |
| Asn | Leu | Ile | Ser | Tyr | Met | Leu | Leu | Met | Lys | Val | Asn | Lys | Asn | Asp | Ile |
| | | | 340 | | | | | 345 | | | | | 350 | | |
| Arg | Lys | Lys | Val | Arg | Arg | Leu | Met | Gly | Lys | Ser | His | Ile | Gly | Leu | Val |
| | | 355 | | | | | 360 | | | | | 365 | | | |
| Tyr | Ser | Gln | Gln | Ile | Asn | Glu | Val | Leu | Asp | Gln | Leu | Ala | Asn | Leu | Asn |
| | 370 | | | | | 375 | | | | | 380 | | | | |
| Gly | Arg | Asp | Leu | Ser | Ile | Trp | Ser | Ser | Gly | Ser | Arg | His | Met | Lys | Lys |
| 385 | | | | | 390 | | | | | 395 | | | | | 400 |
| Gln | Thr | Phe | Val | Val | His | Ala | Gly | Thr | Asp | Thr | Asn | Gly | Asp | Ile | Phe |
| | | | | 405 | | | | | 410 | | | | | 415 | |
| Phe | Met | Glu | Val | Cys | Asp | Asp | Cys | Val | Val | Leu | Arg | Ser | Asn | Ile | Gly |
| | | | 420 | | | | | 425 | | | | | 430 | | |
| Thr | Val | Tyr | Glu | Arg | Trp | Trp | Tyr | Glu | Lys | Leu | Ile | Asn | Met | Thr | Tyr |
| | | | 435 | | | | 440 | | | | | 445 | | | |
| Cys | Pro | Lys | Thr | Lys | Val | Leu | Cys | Leu | Trp | Arg | Arg | Asn | Gly | Ser | Glu |
| | 450 | | | | 455 | | | | | 460 | | | | | |
| Thr | Gln | Leu | Asn | Lys | Phe | Tyr | Thr | Lys | Lys | Cys | Arg | Glu | Leu | Tyr | Tyr |
| 465 | | | | | 470 | | | | | 475 | | | | | 480 |
| Cys | Val | Lys | Asp | Ser | Met | Glu | Arg | Ala | Ala | Ala | Arg | Gln | Gln | Ser | Ile |

|  |  |  | 485 |  |  |  |  | 490 |  |  |  |  | 495 |  |
|---|---|---|---|---|---|---|---|---|---|---|---|---|---|---|
| Lys | Pro | Gly | Pro<br>500 | Glu | Leu | Gly | Gly | Glu<br>505 | Phe | Pro | Val | Gln | Asp<br>510 | Leu | Lys |
| Thr | Gly | Glu<br>515 | Gly | Gly | Leu | Leu | Gln<br>520 | Val | Thr | Leu | Glu | Gly<br>525 | Ile | Asn | Leu |
| Lys | Phe<br>530 | Met | His | Asn | Gln | Val<br>535 | Phe | Ile | Glu | Leu | Asn<br>540 | His | Ile | Lys | Lys |
| Cys<br>545 | Asn | Thr | Val | Arg | Gly<br>550 | Val | Phe | Val | Leu | Glu<br>555 | Glu | Phe | Val | Pro | Glu<br>560 |
| Ile | Lys | Glu | Val | Val<br>565 | Ser | His | Lys | Tyr | Lys<br>570 | Thr | Pro | Met | Ala | His<br>575 | Glu |
| Ile | Cys | Tyr | Ser<br>580 | Val | Leu | Cys | Leu | Phe<br>585 | Ser | Tyr | Val | Ala | Ala<br>590 | Val | His |
| Ser | Ser | Glu<br>595 | Glu | Asp | Leu | Arg | Thr<br>600 | Pro | Pro | Arg | Pro | Val<br>605 | Ser | Ser |

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Asp Tyr Lys Asp Asp Asp Asp Lys
1                     5

TNF RECEPTOR DEATH DOMAIN LIGAND PROTEINS AND METHOD TO IDENTIFY INHIBITORS OF LIGAND BINDING

This application is a continuation-in-part of U.S. application Ser. No. 08/327,514, filed Oct. 19, 1994, now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia et al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nucleotide 2 to nucleotide 931;

(j) a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD ligand protein comprising the amino acid sequence of SEQ ID NO:12;

(p) a polynucleotide encoding an TNF-R1-DD ligand protein comprising a fragment of the amino acid sequence of SEQ ID NO:12; and (q) a polynucleotide capable of hybridizing under stringent conditions to any one of the polynucleotides specified in (a)–(p).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein, which comprises:
(a) growing a culture of the host cell transformed with such polynucleotide compositions in a suitable culture medium; and
(b) purifying the TNF-R1-DD ligand protein from the culture.

The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:
(a) the amino acid sequence of SEQ ID NO:2;
(b) fragments of the amino acid sequence of SEQ ID NO:2;
(c) the amino acid sequence of SEQ ID NO:4;
(d) fragments of the amino acid sequence of SEQ ID NO:4;
(e) the amino acid sequence of SEQ ID NO:6;
(f) fragments of the amino acid sequence of SEQ ID NO:6;
(g) the amino acid sequence of SEQ ID NO:10;
(h) fragments of the amino acid sequence of SEQ ID NO:10;
(i) the amino acid sequence of SEQ ID NO:11; and
(j) fragments of the amino acid sequence of SEQ ID NO:11;
the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:
(a) combining an TNF-R death domain protein with an TNF-R1-DD ligand protein, said combination forming a first binding mixture;
(b) measuring the amount of binding between the TNF-R death domain protein and the TNF-R1-DD ligand protein in the first binding mixture;
(c) combining a compound with the TNF-R death domain protein and an TNF-R1-DD ligand protein to form a second binding mixture;
(d) measuring the amount of binding in the second binding mixture; and
(e) comparing the amount of binding in the first binding mixture with the amount of binding in the second binding mixture;
wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:
(a) the amino acid sequence of SEQ ID NO:2;
(b) fragments of the amino acid sequence of SEQ ID NO:2;
(c) the amino acid sequence of SEQ ID NO:4;
(d) fragments of the amino acid sequence of SEQ ID NO:4;
(e) the amino acid sequence of SEQ ID NO:6;
(f) fragments of the amino acid sequence of SEQ ID NO:6;
(g) the amino acid sequence of SEQ ID NO:8;
(h) fragments of the amino acid sequence of SEQ ID NO:8;
(i) the amino acid sequence of SEQ ID NO:10;
(j) fragments of the amino acid sequence of SEQ ID NO:10;
(k) the amino acid sequence of SEQ ID NO:11; and
(l) fragments of the amino acid sequence of SEQ ID NO:11.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:
(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;
(b) growing the cell in the presence of and in the absence of a compound; and
(c) comparing the degree of expression of the reporter gene in the presence of and in the absence of the compound;
wherein the compound is capable of inhibiting TNF-R death domain binding when a decrease in the degree of expression of the reporter gene occurs. In preferred embodiments, the cell is a yeast cell and the second polynucleotide is selected from the group consisting of:
(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1, which encodes a protein having TNF-R1-DD ligand protein activity;
(c) a polynucleotide encoding an TNF-R1-DD ligand protein comprising the amino acid sequence of SEQ ID NO:2;
(d) a polynucleotide encoding an TNF-R1-DD ligand protein comprising a fragment of the amino acid sequence of SEQ ID NO:2 and having TNF-R1-DD ligand protein activity;
(e) a polynucleotide comprising the nucleotide sequence of SEQ ID NO:3 from nucleotide 2 to nucleotide 415;
(f) a polynucleotide comprising a fragment of the nucleotide sequence of SEQ ID NO:3, which encodes a protein having TNF-R1-DD ligand protein activity;
(g) a polynucleotide encoding an TNF-R1-DD ligand protein comprising the amino acid sequence of SEQ ID NO:4;
(h) a polynucleotide encoding an TNF-R1-DD ligand protein comprising a fragment of the amino acid sequence of SEQ ID NO:4 and having TNF-R1-DD ligand protein activity;
(i) a polynucleotide comprising the nucleotide sequence of SEQ ID NO:5 from nucleotide 2 to nucleotide 559;
(j) a polynucleotide comprising a fragment of the nucleotide sequence of SEQ ID NO:5, which encodes a protein having TNF-R1-DD ligand protein activity;
(k) a polynucleotide encoding an TNF-R1-DD ligand protein comprising the amino acid sequence of SEQ ID NO:6;
(l) a polynucleotide encoding an TNF-R1-DD ligand protein comprising a fragment of the amino acid sequence of SEQ ID NO:6 and having TNF-R1-DD ligand protein activity;
(m) a polynucleotide comprising the nucleotide sequence of SEQ ID NO:7 from nucleotide 57 to nucleotide 875;
(n) a polynucleotide comprising a fragment of the nucleotide sequence of SEQ ID NO:7, which encodes a protein having TNF-R1-DD ligand protein activity;
(o) a polynucleotide encoding an TNF-R1-DD ligand protein comprising the amino acid sequence of SEQ ID NO:8;
(p) a polynucleotide encoding an TNF-R1-DD ligand protein comprising a fragment of the amino acid sequence of SEQ ID NO:8 and having TNF-R1-DD ligand protein activity;
(q) a polynucleotide comprising the nucleotide sequence of SEQ ID NO:9 from nucleotide 2 to nucleotide 931;
(r) a polynucleotide comprising a fragment of the nucleotide sequence of SEQ ID NO:9;
(s) a polynucleotide encoding an TNF-R1-DD ligand protein comprising the amino acid sequence of SEQ ID NO:10;
(t) a polynucleotide encoding an TNF-R1-DD ligand protein comprising a fragment of the amino acid sequence of SEQ ID NO:10;
(u) a polynucleotide comprising the nucleotide sequence of SEQ ID NO:11 from nucleotide 2 to nucleotide 1822;
(v) a polynucleotide comprising a fragment of the nucleotide sequence of SEQ ID NO:11;
(w) a polynucleotide encoding an TNF-R1-DD ligand protein comprising the amino acid sequence of SEQ ID NO:12;

(x) a polynucleotide encoding an TNF-R1-DD ligand protein comprising a fragment of the amino acid sequence of SEQ ID NO:12; and (y) a polynucleotide capable of hybridizing under stringent conditions to any one of the polynucleotides specified in (a)–(x), which encodes a protein having TNF-R1-DD ligand protein activity.

BRIEF DESCRIPTION OF THE DRAWINGS

FIGS. 1 and 2 depict autoradiographs demonstrating the expression of TNF-R1-DD ligand proteins of the present invention.

FIGS. 3(A and B) depicts an autoradiograph demonstrating the expression of clones 1TU, 15TU and 27TU.

FIG. 4 demonstrates the binding of 1TU and 27TU to TNF-R1-DD. MBP, MBP-1TU or MBP-27TU (3 $\mu$g) was incubated with glutathione beads containing 3 $\mu$g of either GST or GST-TNF-R1-DD in 100 $\mu$l of binding buffer (0.2% Triton, 20 mM Tris pH 7.5, 140 mM NaCl, 0.1 mM EDTA, 10 mM DTT and 5% glycerol). The reaction ws performed at 4° C. for 2 hours and centrifuged to remove unbound fraction (Unbound). The beads were then washed with 500 $\mu$l binding buffer four times and resuspended into SDS-sample buffer (Bound). These samples were analyzed by Western blot using anti-MBP antibody (New England Biolab).

FIG. 5 demonstrates the ability of 15TU and 27TU to activate the JNK pathway. COS cells were contransfected with HA-tagged JNK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

DETAILED DESCRIPTION OF THE INVENTION

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD" The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

The sequence of a polynucleotide encoding another such protein is set forth in SEQ ID NO:9 from nucleotides 2 to 931. This polynucleotide has been identified as "clone 1TU" The amino acid sequence of the TNF-R1-DD ligand protein encoded by clone 1TU is set forth in SEQ ID NO:10. It is believed that clone 1TU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASIX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU" The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

The protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO:12). Clone 15TU was deposited with the American Type Culture Collection on Jun. 7, 1995 and given the accession number ATCC 69847. 15TU comprises the same nucleotide sequence as 27TU over this region of amino acids.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-

DD ligand protein is expressed by a host cell which has been transformed (transfected) with the ligated polynucleotide/expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, Hela cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, *Texas Agricultural Experiment Station Bulletin No.* 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include *Saccharomyces cerevisiae, Schizosaccharomyces pombe,* Kluyveromyces strains, Candida, or any yeast strain capable of expressing heterologous proteins. Potentially suitable bacterial strains include *Escherichia coli, Bacillus subtilis, Salmonella typhimurium,* or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl(t or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag SEQ ID NO:13") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_o$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_o$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. No. 4,235,871; U.S. Pat. No. 4,501,728; U.S. Pat. No. 4,837,028; and U.S. Pat. No. 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 μg to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriatc duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer.Chem.Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R1-DD ligand proteins generally.

EXAMPLE 1

CLONING OF TNF-R DEATH DOMAIN LIGAND PROTEIN ENCODING POLYNUCLEOTIDE

A yeast genetic selection method, the "interaction trap" [Gyuris et al, Cell 75:791–803, 1993, which is incorporated herein by reference], was used to screen WI38 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence lexAop-Leu2 in place of the chromosomal LEU2, was transformed with pEG202-TNF-R1-DD and pSH18-34 (Ura+), which carries another reporter sequence, LexAop-lacZ. For screening cDNAs encoding proteins that interact with TNF-R1-DD, the expression vector pJG4-5 (TRP1), containing the WI38 cell cDNA library (see below for the cDNA library construction), was transformed into the above strain (EGY48/pEG202-TNF-R1-DD/pSH18-34) according to the method described by Gietz et al., Nucleic Acids Res., 20:1425 (1992).

cDNA Library Construction:

WI38 cell cDNA library: Double stranded cDNA was prepared from 3 ug of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4-5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1 \times 10^6$ colonies were plated on LB plates containing 100 ug/ml of ampicillin. These $E.coli$ were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results:

$1 \times 10^6$ transformants were obtained on glucose Ura⁻His⁻Trp⁻ plates. These transformants were pooled and resuspended in a solution of 65% glycerol, 10 mM Tris-HCl (pH 7.5), 10 mM $MgCl_2$ and stored at $-80°$ C. in 1 mL aliquots. For screening purposes, aliquots of these were diluted 10-fold into Ura⁻His⁻Trp⁻ CM dropout gal/raff medium (containing 2% galactose, 1% raffinose), which induces the expresssion of the library encoded proteins, and incubated at 30° C. for 4 hours. $12 \times 10^6$ colony forming units (CFUs) were then plated on standard 10 cm galactose X-Gal Ura⁻His⁻Trp⁻Leu⁻ plates at a density of $2 \times 10^5$ CFU/plate. After three days at 30° C., about 1,000 colonies were formed (Leu⁺) and of those, sixty-four colonies were LacZ⁺. In order to test if the Leu⁺/LacZ⁺ phenotype was due to the library-encoded protein, the galactose dependency of the phenotype was tested. Expression of the library-encoded proteins was turned off by growth on glucose Ura⁻His⁻Trp⁻ master plates and then retested for galactose-dependency on glucose Ura⁻His⁻Trp⁻Leu⁻, galactose Ura⁻His⁻Trp⁻Leu⁻, glucose X-Gal Ura⁻His⁻Trp⁻, and galactose X-Gal Ura⁻His⁻Trp⁻ plates. Of these, 32 colonies showed galactose-dependent growth on Leu⁻ plates and galactose-dependent blue color on X-Gal-containing medium (LacZ⁺ phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4-5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4-5 containing these clones sequences were rescued from yeast by transforming the total yeast DNAs into the $E.$ $coli$ strain KC8 and selecting for growth on Trp-ampicillin plates. These putative TNFR1 interacting proteins were then tested further for specificity of interaction with the TNF-R1-DD by the reintroduction of JG4-5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results:

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones, 15TU and 27TU, encode related or identical sequences, except that 27TU contains about 864 additional nucleotides (or about 288 amino acids) at the 5' end. 15/27TU also encode a novel sequence.

EXAMPLE 2

EXPRESSION OF THE TNF-R1-DD ligand PROTEIN cDNAs encoding TNF-R intracellular ligand proteins were released from the pJG4-5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in $E.$ $coli$, a pED-based vector for mammalian expression, and pVL or pBlue-BacHis (Invitrogen) for baculovirus/insect expression. For the immunodetection of TNF-R intracellular ligand expression in mammalian cells, an epitope sequence, "Flag," (SEQ ID NO:13) was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys (SEQ ID NO:13). Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide (SEQ ID NO:13), can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

Figure 2:
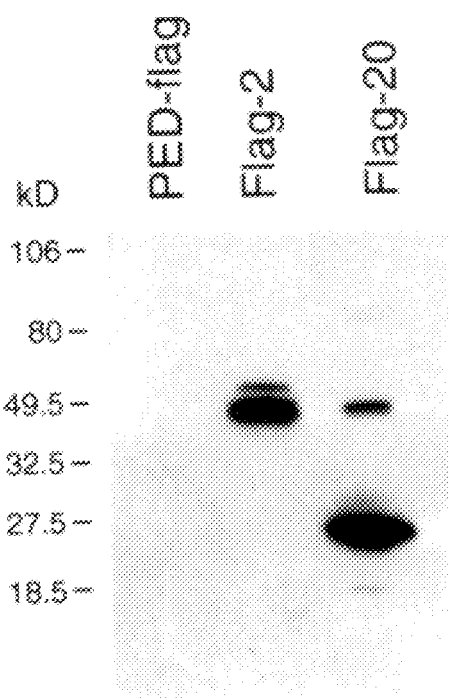

FIGS. 1 and 2 depict autoradiographs demonstrating the expression of TNF-R1-DD ligand proteins in yeast and mammalian cells. FIG. 1 shows the results of expression of isolated clones of the present invention in yeast. EGY48 was transformed with pJG4-5 containing clone 2DD, 3DD or 20DD. Cells were then grown overnight in the galactose/raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty μg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

ASSAYS OF TNF-R DEATH DOMAIN BINDING

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, N.Y., 1990 (by Rose, M. D., Winston, F., and Hieter, P.).

The second assay for measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GSY-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

CHARACTERIZATION OF TNF-R DEATH DOMAIN LIGAND PROTEIN

Mapping the interaction site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-mediated response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or functional assays

The signal transduction events initiated by TNF binding to its receptor are still largely unknown. However, one major result of TNF binding is the stimulation of cellular serine/threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

ISOLATION OF FULL LENGTH CLONES

In many cases, cDNAs obtained from the interaction trap method each encode only a portion of the full length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

ANTIBODIES SPECIFIC FOR TNF-R INTRACELLULAR LIGAND PROTEIN

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

CHARACTERIZATION OF CLONES 1TU AND 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $p75_{IC}$), the entire intracellular domain of TNF-R (TNF-R $P55_{IC}$), the death domain of the fas antigen (which shares 28% identity with TNF-R-DD) ($Fas_{DD}$), the Drosophila transcription factor bicoid, and a region of the IL-1 receptor known to be critical for signalling ($IL-1R_{477-527}$). As shown in Table 1, none of these clones interacted with TNF-R $p75_{IC}$ or $Fas_{DD}$, and only 1TU interacted with bicoid. In contrast, both 1TU and 15TU bound the cytoplasmic domain of the p55 TNF-R, as well as residues 477–527 of the IL-1R. 27TU interacted relatively weakly with these sequences.

TABLE 1

| clone | TNF-R$_{DD}$ | TNF-R p75$_{1C}$ | TNF-R p55$_{1C}$ | Fas$_{DD}$ | bicoid | IL-1R (477–527) |
|---|---|---|---|---|---|---|
| 1TU | +++ | − | +++ | − | ++ | +++ |
| 15TU | +++ | ± | +++ | − | − | ++ |
| 27TU | +++ | − | + | − | − | + |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | TNF-R$_{DD}$ | F345A | L351A | W378A | I408A |
|---|---|---|---|---|---|
| 1TU | +++ | + | ++ | ++ | + |
| 15TU | +++ | + | + | ++ | ++ |
| 27TU | +++ | + | + | ± | ++ |

Expression of 1TU, 15TU and 27TU

Figure 3A:
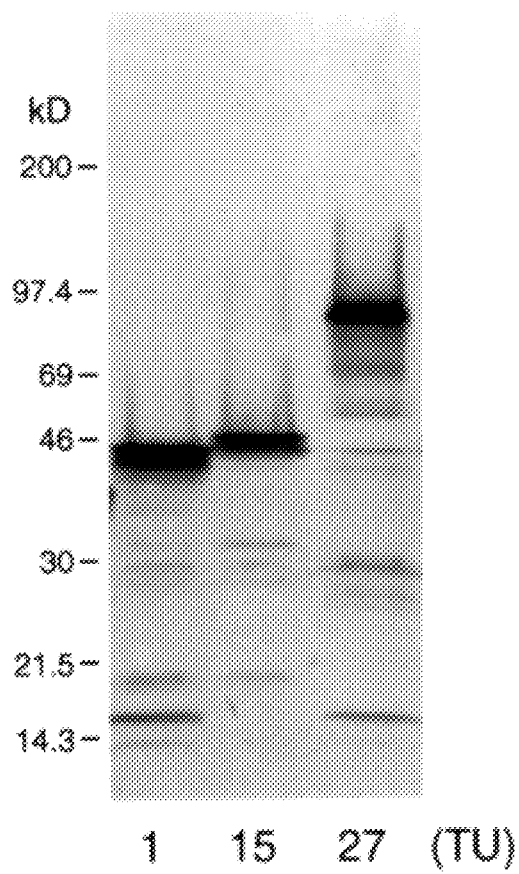
Figure 3B:
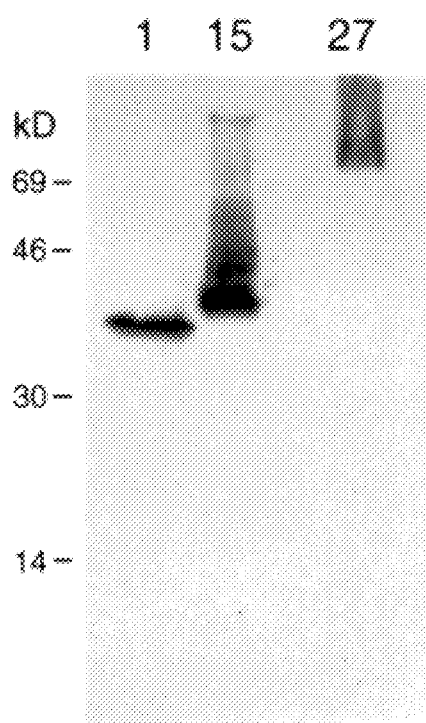

FIG. 3 depicts an autoradiograph demonstrating the expression of clones 1TU, 15TU and 27TU in yeast (A) and COS cells (B).

In (A): EGY48 was transformed with pJG4-5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

Figure 4:
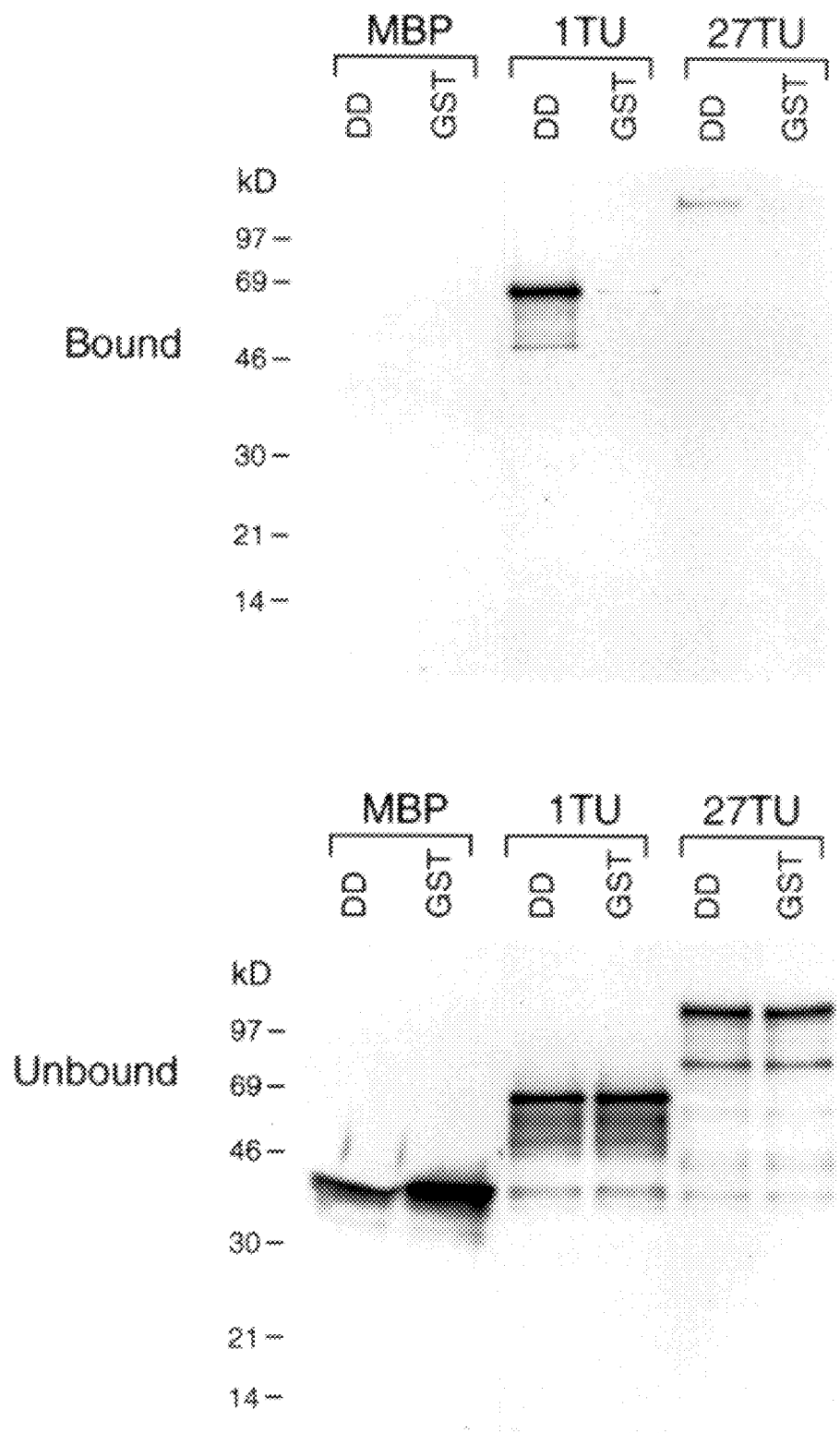

The interaction of 1TU and 27TU with TNF-R1-DD was tested using purified bacterially expressed fusion proteins. As shown in FIG. 4, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation of JNK Activity

Figure 5:
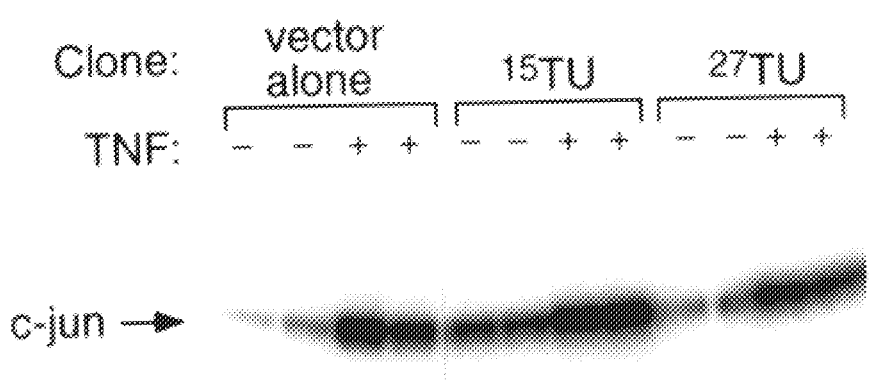

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

What is claimed is:

1. A method of identifying an inhibitor of TNF-R1 death domain binding which comprises:
    (a) combining a TNF-R1 death domain protein with a composition comprising a TNF-R1-DD intracellular ligand protein, said combination forming a first binding mixture;
    (b) measuring the amount of binding between the TNF-R1 death domain protein and the TNF-R1-DD ligand protein in the first binding mixture;
    (c) combining a compound with the TNF-R1 death domain protein and a TNF-R1-DD intracellular ligand protein to form a second binding mixture;
    (d) measuring the amount of binding in the second binding mixture; and
    (e) comparing the amount of binding in the first binding mixture with the amount of binding in the second binding mixture;
wherein the compound is capable of inhibiting TNF-R1 death domain binding when a decrease in the amount of binding of the second binding mixture occurs.

2. The method of claim 1 wherein said TNF-R1-DD intracellular ligand protein comprises an amino acid sequence selected from the group consisting of:
    (a) the amino acid sequence of SEQ ID NO:2; and
    (b) fragments of the amino acid sequence of SEQ ID NO:2 having TNF-R1-DD ligand protein activity.

3. The method of claim 1 wherein said TNF-R1-DD intracellular ligand protein comprises an amino acid sequence selected from the group consisting of:
    (a) the amino acid sequence of SEQ ID NO:10;
    (b) fragments of the amino acid sequence of SEQ ID NO:10 having TNF-R1-DD ligand protein activity;
    (c) the amino acid sequence of SEQ ID NO:12; and
    (d) fragments of the amino acid sequence of SEQ ID NO:12 having TNF-R1-DD ligand protein activity.

4. The method of claim 1 wherein said TNF-R1-DD intracellular ligand protein comprises the amino acid sequence of SEQ ID NO:2.

5. The method of claim 1 wherein said TNF-R1-DD intracellular ligand protein comprises the amino acid sequence of SEQ ID NO:10.

6. The method of claim 1 wherein said TNF-R1-DD intracellular ligand protein comprises the amino acid sequence of SEQ ID NO:12.

* * * * *